(12) United States Patent
Schwartz et al.

(10) Patent No.: US 11,039,888 B2
(45) Date of Patent: Jun. 22, 2021

(54) CALCULATION OF AN ABLATION PLAN

(71) Applicant: Navix International Limited, Tortola (VG)

(72) Inventors: Yitzhack Schwartz, Haifa (IL); Zalman Ibragimov, Rehovot (IL); Yehonatan Ben David, Tel-Aviv (IL); Eli Dichterman, Haifa (IL)

(73) Assignee: Navix International Limited, Road Town (VG)

( * ) Notice: Subject to any disclaimer, the term of this patent is extended or adjusted under 35 U.S.C. 154(b) by 493 days.

(21) Appl. No.: 15/570,341

(22) PCT Filed: May 11, 2016

(86) PCT No.: PCT/IB2016/052688
§ 371 (c)(1),
(2) Date: Oct. 29, 2017

(87) PCT Pub. No.: WO2016/181317
PCT Pub. Date: Nov. 17, 2016

(65) Prior Publication Data
US 2018/0325597 A1    Nov. 15, 2018

Related U.S. Application Data

(60) Provisional application No. 62/160,080, filed on May 12, 2015, provisional application No. 62/291,065, (Continued)

(51) Int. Cl.
*G06F 30/20* (2020.01)
*A61B 34/10* (2016.01)
(Continued)

(52) U.S. Cl.
CPC ............ *A61B 34/10* (2016.02); *A61B 5/0538* (2013.01); *A61B 5/063* (2013.01); (Continued)

(58) Field of Classification Search
CPC ......... G06F 17/18; G06F 30/20; G01H 17/00; H02J 2203/20; H02K 7/1823
See application file for complete search history.

(56) References Cited

U.S. PATENT DOCUMENTS 4,917,097 A    4/1990    Proudian et al.
5,553,611 A    9/1996    Budd et al.
(Continued)

FOREIGN PATENT DOCUMENTS

EP    1504713    2/2005
EP    1726268    11/2006
(Continued)

OTHER PUBLICATIONS

International Preliminary Report on Patentability dated Nov. 23, 2017 From the International Bureau of WIPO Re. Application No. PCT/IB2016/052686. (11 Pages).
(Continued)

*Primary Examiner* — Kibrom K Gebresilassie

(57) ABSTRACT

Systems and methods are described for planning of catheter ablation procedures, and in particular for planning of the placement of lesions and/or parameters used in ablation. In some embodiments, planning is based on thermal and/or dielectric simulation of lesions, individualized to the anatomy of the particular patient. Optionally, a plan comprises planning of a path along which an ablation lesion is to be formed, the ablation lesion optionally comprising one or more sub-lesions. The plan is optionally optimized for one or more criteria including, for example: minimization of path length, minimization of sub-lesion number, simplification of catheter maneuvering, avoidance of collateral damage to non-target tissue, access to the target dependent on
(Continued)

anatomy shape and/or catheter mechanics, and/or features of the target anatomy such as tissue wall thickness and/or fiber direction.

26 Claims, 15 Drawing Sheets

Related U.S. Application Data filed on Feb. 4, 2016, provisional application No. 62/304,455, filed on Mar. 7, 2016.

(51) Int. Cl.
| | |
|---|---|
| A61B 5/0538 | (2021.01) |
| A61B 5/06 | (2006.01) |
| A61B 18/14 | (2006.01) |
| A61B 90/00 | (2016.01) |
| G06F 30/00 | (2020.01) |
| A61B 34/20 | (2016.01) |
| G16H 50/50 | (2018.01) |
| G16H 10/60 | (2018.01) |
| G16H 30/20 | (2018.01) |
| A61B 18/00 | (2006.01) |
| A61B 17/00 | (2006.01) |
| H02K 7/18 | (2006.01) |
| G06F 17/18 | (2006.01) |
| G01H 17/00 | (2006.01) |
| A61M 25/01 | (2006.01) |

(52) U.S. Cl.
CPC .......... *A61B 18/1492* (2013.01); *A61B 34/20* (2016.02); *A61B 90/37* (2016.02); *G06F 30/00* (2020.01); *G06F 30/20* (2020.01); *G16H 10/60* (2018.01); *G16H 30/20* (2018.01); *G16H 50/50* (2018.01); *A61B 90/39* (2016.02); *A61B 2017/00026* (2013.01); *A61B 2018/00357* (2013.01); *A61B 2018/00577* (2013.01); *A61B 2018/00642* (2013.01); *A61B 2018/00702* (2013.01); *A61B 2018/00738* (2013.01); *A61B 2018/00761* (2013.01); *A61B 2018/00791* (2013.01); *A61B 2018/00875* (2013.01); *A61B 2018/00904* (2013.01); *A61B 2034/104* (2016.02); *A61B 2034/105* (2016.02); *A61B 2034/107* (2016.02); *A61B 2034/2046* (2016.02); *A61B 2034/2053* (2016.02); *A61B 2090/065* (2016.02); *A61B 2090/365* (2016.02); *A61B 2090/374* (2016.02); *A61B 2090/3762* (2016.02); *A61B 2090/3983* (2016.02); *A61M 2025/0166* (2013.01); *G01H 17/00* (2013.01); *G06F 17/18* (2013.01); *H02J 2203/20* (2020.01); *H02K 7/1823* (2013.01)

(56) References Cited

U.S. PATENT DOCUMENTS

| | | | |
|---|---|---|---|
| 5,662,108 A | 9/1997 | Budd et al. | |
| 5,697,377 A | 12/1997 | Wittkampf | |
| 5,724,978 A | 3/1998 | Tenhoff | |
| 5,983,126 A | 11/1999 | Wittkampf | |
| 6,019,725 A | 2/2000 | Vesely et al. | |
| 6,038,468 A | 3/2000 | Rex | |
| 6,240,307 B1 | 5/2001 | Beatty et al. | |
| 6,317,621 B1 | 11/2001 | Graumann et al. | |
| 6,322,558 B1 | 11/2001 | Taylor et al. | |
| 6,515,657 B1 | 2/2003 | Zanelli | |
| 6,640,119 B1 | 10/2003 | Budd et al. | |
| 6,728,562 B1 | 4/2004 | Budd et al. | |
| 6,826,420 B1 | 11/2004 | Beatty et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,146,210 B2 * | 12/2006 | Palti | A61N 1/0408 607/2 |
| 7,187,973 B2 | 3/2007 | Hauck | |
| 7,189,208 B1 | 3/2007 | Beatty et al. | |
| 7,996,060 B2 | 8/2011 | Trofimov et al. | |
| 8,556,888 B2 * | 10/2013 | Nields | A61B 18/1815 606/27 |
| 9,955,946 B2 * | 5/2018 | Miller | A61B 8/0841 |
| 9,980,653 B2 * | 5/2018 | Lichtenstein | G06T 11/206 |
| 2002/0068931 A1 | 6/2002 | Wong et al. | |
| 2003/0074011 A1 | 4/2003 | Gilboa et al. | |
| 2003/0220636 A1 | 11/2003 | Bowman et al. | |
| 2004/0039278 A1 | 2/2004 | Wacker et al. | |
| 2004/0044279 A1 | 3/2004 | Lewin et al. | |
| 2004/0097805 A1 | 5/2004 | Verard et al. | |
| 2004/0176804 A1 * | 9/2004 | Palti | A61N 1/0408 607/2 |
| 2005/0015006 A1 | 1/2005 | Mitschke et al. | |
| 2005/0033164 A1 | 2/2005 | Yatsuo et al. | |
| 2005/0054913 A1 | 3/2005 | Duerk et al. | |
| 2005/0054918 A1 | 3/2005 | Sra | |
| 2005/0245814 A1 | 11/2005 | Anderson et al. | |
| 2007/0043296 A1 * | 2/2007 | Schwartz | A61B 8/12 600/463 |
| 2007/0167706 A1 | 7/2007 | Boese et al. | |
| 2007/0167726 A1 | 7/2007 | Unal et al. | |
| 2008/0114235 A1 | 5/2008 | Unal et al. | |
| 2008/0118135 A1 | 5/2008 | Averbuch et al. | |
| 2008/0125775 A1 | 5/2008 | Morris | |
| 2008/0177175 A1 | 7/2008 | Mottola et al. | |
| 2008/0183070 A1 | 7/2008 | Unal et al. | |
| 2008/0208031 A1 | 8/2008 | Kurpad et al. | |
| 2008/0221425 A1 | 9/2008 | Olson et al. | |
| 2008/0275440 A1 | 11/2008 | Kratoska et al. | |
| 2008/0275465 A1 | 11/2008 | Paul et al. | |
| 2009/0015818 A1 | 1/2009 | Ikeda et al. | |
| 2009/0076499 A1 * | 3/2009 | Azure | A61N 1/05 606/41 |
| 2009/0148012 A1 | 6/2009 | Altmann et al. | |
| 2009/0275828 A1 | 11/2009 | Shachar et al. | |
| 2009/0281566 A1 | 11/2009 | Edwards et al. | |
| 2010/0063400 A1 | 3/2010 | Hall et al. | |
| 2010/0185087 A1 * | 7/2010 | Nields | A61B 18/18 600/439 |
| 2010/0217116 A1 | 8/2010 | Eck et al. | |
| 2010/0249579 A1 | 9/2010 | Starks | |
| 2010/0274239 A1 | 10/2010 | Paul et al. | |
| 2010/0283484 A1 | 11/2010 | Cohen et al. | |
| 2010/0312094 A1 | 12/2010 | Guttman et al. | |
| 2011/0106221 A1 | 5/2011 | Neal, II et al. | |
| 2011/0230758 A1 | 9/2011 | Eichler | |
| 2012/0059249 A1 | 3/2012 | Verard et al. | |
| 2012/0109115 A1 | 5/2012 | Condie et al. | |
| 2012/0123250 A1 | 5/2012 | Pang et al. | |
| 2012/0172724 A1 | 7/2012 | Hill et al. | |
| 2012/0173217 A1 | 7/2012 | Heimbecher | |
| 2012/0197243 A1 | 8/2012 | Sherman et al. | |
| 2012/0238866 A1 | 9/2012 | Wang et al. | |
| 2013/0137980 A1 | 5/2013 | Waters et al. | |
| 2013/0272593 A1 | 10/2013 | Lee et al. | |
| 2014/0088943 A1 | 3/2014 | Trayanova et al. | |
| 2014/0187949 A1 * | 7/2014 | Zhao | A61B 8/12 600/443 |
| 2014/0330111 A1 * | 11/2014 | Lichtenstein | G06T 11/206 600/424 |
| 2018/0125575 A1 * | 5/2018 | Schwartz | A61B 34/20 |

(56) References Cited

U.S. PATENT DOCUMENTS

2018/0325597 A1* 11/2018 Schwartz ............. A61B 5/0538
2020/0022649 A1* 1/2020 Rodriguez ........... A61B 5/0538

FOREIGN PATENT DOCUMENTS

| EP | 2777584 | 9/2014 |
|----|---------|--------|
| HR | P20131208 | 3/2014 |
| JP | 2001-340336 | 12/2001 |
| WO | WO 98/01069 | 1/1998 |
| WO | WO 2007/067628 | 6/2007 |
| WO | WO 2010/102794 | 9/2010 |
| WO | WO 2016/181315 | 11/2016 |
| WO | WO 2016/181316 | 11/2016 |
| WO | WO 2016/181317 | 11/2016 |
| WO | WO 2016/181318 | 11/2016 |
| WO | WO 2016/181320 | 11/2016 |
| WO | WO 2018/011757 | 1/2018 |

OTHER PUBLICATIONS

International Preliminary Report on Patentability dated Nov. 23, 2017 From the International Bureau of WIPO Re. Application No. PCT/IB2016/052687. (10 Pages).
International Preliminary Report on Patentability dated Nov. 23, 2017 From the International Bureau of WIPO Re. Application No. PCT/IB2016/052688. (9 Pages).
International Preliminary Report on Patentability dated Nov. 23, 2017 From the International Bureau of WIPO Re. Application No. PCT/IB2016/052690. (9 Pages).
International Preliminary Report on Patentability dated Nov. 23, 2017 From the International Bureau of WIPO Re. Application No. PCT/IB2016/052692. (13 Pages).
International Search Report and the Written Opinion dated Oct. 21, 2016 From the International Searching Authority Re. Application No. PCT/IB2016/052687. (16 Pages).
Communication Relating to the Results of the Partial International Search dated Aug. 22, 2016 From the International Searching Authority Re. Application No. PCT/IB2016/052686.
Communication Relating to the Results of the Partial International Search dated Aug. 22, 2016 From the International Searching Authority Re. Application No. PCT/IB2016/052688.
Communication Relating to the Results of the Partial International Search dated Aug. 25, 2016 From the International Searching Authority Re. Application No. PCT/IB2016/052692.
Communication Relating to the Results of the Partial International Search dated Aug. 26, 2016 From the International Searching Authority Re. Application No. PCT/IB2016/052687.
International Search Report and the Written Opinion dated Jan. 3, 2017 From the International Searching Authority Re. Application No. PCT/IB2016/052688. (14 Pages).
International Search Report and the Written Opinion dated Oct. 12, 2016 From the International Searching Authority Re. Application No. PCT/IB2016/052686.
International Search Report and the Written Opinion dated Oct. 16, 2017 From the International Searching Authority Re. Application No. PCT/IB2017/054263. (16 Pages).
International Search Report and the Written Opinion dated Oct. 17, 2016 From the International Searching Authority Re. Application No. PCT/IB2016/052692.
International Search Report and the Written Opinion dated Aug. 25, 2016 From the International Searching Authority Re. Application No. PCT/IB2016/052690.
Anter et al. "Evaluation of a Novel High-Resolution Mapping Technology for Ablation of Recurrent Scar-Related Atrial Tachycardias," Heart Rhythm, 13(10): 2048-2055, Oct. 2016.
Arujuna et al. "Acute Pulmonary Vein Isolation Is Achieved by a Combination of Reversible and Irreversible Atrial Injury After Catheter Ablation: Evidence From Magnetic Resonance Imaging", Circulation: Arrhythmia and Electrophysiology, 5(4): 691-700, Published Online May 31, 2012.
Black-Maier et al. "Risk of Atrioesophageal Fistula Formation With Contact-Force Sensing Catheters", HeartRhythm, 14(9): 1328-1333, Published Online Apr. 15, 2017.
Bourier et al. "Electromagnetic Contact-Force Sensing Electrophysiological Catheters: How Accurate Is the Technology?", Journal of Cardiovascular Electrophysiology, 27(3): 347-350, Published Online Jan. 16, 2016.
Bourier et al. "Fiberoptic Contact-Force Sensing Electrophysiological Catheters: How Precise Is Technology?", Journal of Cardiovascular Electrophysiology, 28(1): 109-114, Published Online Oct. 24, 2016.
Chierchia et al. "An Initial Clinical Experience With a Novel Microwave Radiometry Sensing Technology Used in Irrigated RF Ablation for Flutter", Academic Hospital Brussels, Belgium, 1 P. Jan. 1, 2011.
Deno et al. "Measurement of Electrical Coupling Between Cardiac Ablation Catheters and Tissue", IEEE Transactions on Biomedical Engineering, 61(3): 765-774, Published Online Nov. 6, 2013.
Eyerly et al. "The Evolution of Tissue Stiffness at Radiofrequency Ablation Sites During Lesions Formation and in the Peri-Ablation Period", Journal of Cardiovascular Electrophysiology, 26(9): 1009-1018, Sep. 2015.
Gabriel "Compilation of the Dielectric Properties of Body Tissues at RF and Microwave Frequencies", Occupational and Environmental Health Directorate, Radiofrequency Radiation Division, Brooks Air Force Base, Texas, USA, Technical Report for the Period Sep. 15, 1993-Dec. 14, 1994, p. 1-16, Jan. 1996.
Gaspar et al. "Use of Electrical Coupling Information (ECI) in AF Catheter Ablation: A Prospective Randomized Pilot Study", HeartRhythm, 10(2): 176-181, Feb. 2013.
General Electric "CardEP: Streamlined Post-Processing for Enhanced Electrophysiology Procedures", General Electric Company, GE Healthcare, Product Description, 2 P., 2016.
Grace "Modifying PVI Lines to Incorporate Non-PV Targets Identified by Pre-Ablation Mapping with the AcQMap System: Update on the UNCOVER-AF Trial," EP Lab Digest, 17(5), May 2017, 5 pages.
Ikeda et al. "Microwave Volumetric Temperature Sensor Improves Control of Radiofrequency Lesion Formation and Steam Pop", 33rd Annual Scientific Sessions, Heart Rhythm, Boston, MA, USA, May 9-12, 2012, Session: Role of Autonomics in Catheter Ablation, # AB13-05, May 10, 2012.
Ikeda et al. "Novel Irrigated Radiofrequency Ablation Catheter With Microwave Volumetric Temperature Sensor Predicts Lesion Size and Incidence of Steam Pop in Canine Beating Heart", 33rd Annual Scientific Sessions, Heart Rhythm, Boston, MA, USA, May 9-12, 2012, Poster Session III, # PO3-53, May 10, 2012.
Lardo et al. "Visualization and Temporal/Spatial Characterization of Cardiac Radiofrequency Ablation Lesions Using Magnetic Resonance Imaging", Circulation, 102(6): 698-705, Aug. 8, 2000.
Lemola et al. "Computed Tomographic Analysis of the Anatomy of the Left Atrium and the Esophagus. Implications for Left Atrial Catheder Ablation", Circulation, 110(24): 3655-3660, Published Online Nov. 29, 2004.
Lunak "12 510(k) FDA Summary for Public Disclosure", St. Jude Medical, Section 12, 6 P., Aug. 29, 2013.
Myronenko et al. "Non-Rigid Point Set Registration: Coherent Point Drift", Advances in Neural Information Processing Systems, NIPS, 19: 1009-1016, 2009.
Pappone "Carto 3", AF-Ablation, Arrhythmology and Cardiac Electrophysiology Department, 1 P., 2009.
Perazzi et al. "Panoramic Video From Unstructured Camera Arrays", Computer Graphics Forum, 34(2): 57-68, May 2015.
Piorkowski et al. "First in Human Validation of Impedance-Based Catheter Tip-to-Tissue Contact Assessment in the Left Atrium", Study of Clinical Results, Poster, Journal of Cardiovascular Electrophysiology, 20(12): 1366-1373, Published Online Jul. 7, 2009.

(56) References Cited

OTHER PUBLICATIONS

Sanchez-Quintana et al. "Anatomic Relations Between the Esophagus and Left Atrium and Relevance for Ablation of Atrial Fibrillation", Circulation, 112(10): 1401-1406, Published Online Aug. 29, 2005.

St. Jude Medical "Cardiac Mapping System / ECG. NSite™ NavX™" St. Jude Medical, Products Sheet, 22 P., 2017.

Vandekerckhove et al. "Flutter Ablation With an irrigated Catheter Using Microwave Radiometry Sensing Technology: First Report in Men", Sint Jan Hospital, Department of Cardiology, Bruges, Belgium, 1 P., Jan. 1, 2011.

Wang et al. "Microwave Radiometric Thermoetry and Its Potential Applicability to Ablative Therapy", Journal of Interventional Cardiac Electrophysiology, 4(1): 295-300, Feb. 2000.

Wittkampf et al. "LocaLisa: New Technique for Real-Time 3-Dimensional Localization of Regular Intracardiac Electrodes", Circulation, 99(10): 1312-1317, Mar. 16, 1999.

Zhong et al. "On the Accuracy of CartoMerge for Guiding Posterior Left Atrial Ablation in Man", Heart Rhythm, 4(5): 595-602, Published Online Feb. 9, 2007.

\* cited by examiner

CALCULATION OF AN ABLATION PLAN

RELATED APPLICATIONS

This application is a National Phase of PCT Patent Application No. PCT/IB2016/052688 having International filing date of May 11, 2016, which claims the benefit of priority under 35 USC § 119(e) of U.S. Provisional Patent Application Nos. 62/160,080 filed on May 12, 2015; 62/291,065 on filed Feb. 4, 2016; and 62/304,455 filed on Mar. 7, 2016. The contents of the above applications are all incorporated by reference as if fully set forth herein in their entirety.

PCT Patent Application No. PCT/IB2016/052688 is also related to PCT Patent Application Nos. PCT/IB2016/052690, titled "LESION ASSESSMENT BY DIELECTRIC PROPERTY ANALYSIS", PCT/IB2016/052687 titled "SYSTEMS AND METHODS FOR TRACKING AN INTRABODY CATHETER", PCT/IB2016/052692 titled "FIDUCIAL MARKING FOR IMAGE-ELECTROMAGNETIC FIELD REGISTRATION", and PCT/IB2016/052686 titled "CONTACT QUALITY ASSESSMENT BY DIELECTRIC PROPERTY ANALYSIS", all having the International filing date of May 11, 2016.

FIELD AND BACKGROUND OF THE INVENTION

The present invention, in some embodiments thereof, relates to systems and methods for treatment with intrabody catheters and, more particularly, but not exclusively, to systems and methods for planning and/or dynamically adjusting planning of treatments such as ablation treatments performed using intrabody catheters.

Catheterized intra-body ablation probes (for example, RF ablation probes) are in use for minimally invasive ablation procedures. Such procedures are performed, for example, in the treatment of cardiac arrhythmia. In the control of cardiac arrhythmia, a goal of ablation is to create lesions in a pattern which will break pathways of abnormal electrophysiological conduction which contribute to heart dysfunction (such as atrial fibrillation).

Single procedure success rates of catheter ablation at one year appear variable. For example, they have been reported at 15%-60% (Sohns et al., Catheter Contact Force: A Review of Emerging Techniques and Technologies in AF Ablation. Journal Innov Cardiac Rhythm Management, 2014 5:1773-1780).

Earlier time post-procedure success percentages are generally higher. Gaps in the ablation line have been reported to contribute to restoration of impulse conduction (Ouyang et al., Recovered pulmonary vein conduction as a dominant factor for recurrent atrial tachyarrhythmias after complete circular isolation of the pulmonary veins: lessons from double Lasso technique. Circulation. 2005; 111: 127-135).

One form of catheter ablation known as RF ablation relies on heating caused by the interaction between a high-frequency alternating current (e.g., 350-500 kHz) introduced to a treatment region, and dielectric properties of material (e.g., tissue) in the treatment region. One variable affecting the heating is the frequency-dependent relative permittivity κ of the tissue being treated. The (unitless) relative permittivity of a material (herein, κ or dielectric constant) is a measure of how the material acts to reduce an electrical field imposed across it (storing and/or dissipating its energy). Relative permittivity is commonly expressed as $$\kappa = \varepsilon_r(\omega) = \frac{\varepsilon(\omega)}{\varepsilon_0},$$

where $\omega=2\pi f$, and f is the frequency (of an imposed voltage signal). In general, $\varepsilon_r(\omega)$ is complex valued; that is: $\varepsilon_r(\omega)=\varepsilon'_r(\omega)+i\varepsilon''_r(\omega)$.

The real part $\varepsilon'_r(\omega)$ is a measure of how energy of an applied electrical field is stored in the material (at a given electrical field frequency), while the imaginary part $\varepsilon''_r(\omega)$ is a measure of energy dissipated. It is this dissipated energy that is converted, for example, into heat for ablation. Loss in turn is optionally expressed as a sum of dielectric loss $E''_{rd}$ and conductivity σ as $$\varepsilon''_r(\omega) = \varepsilon''_{rd} + \frac{\sigma}{\omega \cdot \varepsilon_0}.$$

Any one of the above parameters: namely κ, ε, $\varepsilon'_r$, $\varepsilon''_r$, σ, and/or $\varepsilon''_{rd}$, may be referred to herein as a dielectric parameter. The term dielectric parameter encompasses also parameters that are directly derivable from the above-mentioned parameters, for example, loss tangent, expressed as tan $$\sigma = \frac{\varepsilon''_r}{\varepsilon'_r},$$

complex refractive index, expressed as $n=\sqrt{\varepsilon_r}$, and impedance, expressed as $$Z(\omega) = \sqrt{\frac{i\omega}{\sigma + i\omega\varepsilon_r}} \text{ (with } i = \sqrt{-1}\text{)}.$$

Herein, a value of a dielectric parameter of a material may be referred to as a dielectric property of the material. For example, having a relative permittivity of about 100000 is a dielectric property of a 0.01 M KCl solution in water at a frequency of 1 kHz, at about room temperature (20°, for example; it should be noted that some dielectric properties exhibit temperature dependence). Optionally, a dielectric property more specifically comprises a measured value of a dielectric parameter. Measured values of dielectric parameters are optionally provided relative to the characteristics (bias and/or jitter, for example) of a particular measurement circuit or system. Values provided by measurements should be understood to comprise dielectric properties, even if influenced by one or more sources of experimental error. The formulation "value of a dielectric parameter" is optionally used, for example, when a dielectric parameter is not necessarily associated with a definite material (e.g., it is a parameter that takes on a value within a data structure).

Dielectric properties as a function of frequency have been compiled for many tissues, for example, C. Gabriel and S. Gabriel: *Compilation of the Dielectric Properties of Body Tissues at RF and Microwave Frequencies* (web pages presently maintained at //niremf(dot)ifac(dot)cnr(dot)it/docs/DIELECTRIC/home(dot)html).

SUMMARY OF THE INVENTION

There is provided, in accordance with some exemplary embodiments, a method for planning an ablation plan of a target tissue in a patient, the method comprising: receiving data characterizing patient-specific anatomy comprising at least the target tissue, wherein the data include data on dielectric properties associated with the target tissue; calculating by computer simulated results of one or more operations to lesion the target tissue, based on the received data; producing a planned target form of the lesion, wherein the planned target form is selected based on one or more criteria evaluated on the simulated results; and providing an indication of the planned target form.

According to some embodiments, the data include data on thermal properties associated with the target tissue.

According to some embodiments, the method comprises producing an ablation plan for producing the planned target form.

According to some embodiments, the received data characterize geometry of the target anatomical structure, and the ablation plan describes the adjustment of parameters of ablation as a function of geometry along the planned target form of the lesion.

According to some embodiments, the parameters of ablation are adjusted as a function of structure thickness along the planned target form of the lesion.

According to some embodiments, the received data characterize a structural anisotropy as a function of position in the target anatomical structure, and the ablation plan is produced based on consideration of the structural anisotropy.

According to some embodiments, the anisotropy comprises an orientation of myocardial fibers in the target anatomical structure.

According to some embodiments, the received data characterize the positions of at least one existing lesion in the target anatomical structure, and the planned target form is adjusted to incorporate the at least one existing lesion.

According to some embodiments, the target anatomical structure comprises a cardiac wall.

According to some embodiments, the cardiac wall is a wall of an atrial heart chamber, and the planned target form of the lesion is selected for the blockage of cardiac muscle contractile impulses contributing to atrial fibrillation, based on the computer simulated results of one or more operations to lesion the target tissue.

According to some embodiments, the simulated results comprise thermal simulation of the effect of lesioning on the patient-specific anatomy, based on thermal characteristics associated with the patient-specific anatomy.

According to some embodiments, the planned target form of the lesion is selected for transmural ablation of the target tissue, while avoiding collateral damage to tissue in thermal contact with the target tissue.

According to some embodiments, the simulated results comprise dielectric simulation of the effect of lesioning on the patient-specific anatomy, based on dielectric properties associated with the patient-specific anatomy.

According to some embodiments, the patient-specific anatomy further comprises non-target anatomical structure adjacent to the target anatomical structure.

According to some embodiments, the calculating comprises simulation of lesion effects on one or more non-target anatomical structures, and the planned target form is adjusted to avoid lesioning of the non-target anatomical structure.

According to some embodiments, the non-target anatomical structure comprises at least one from the group consisting of: a portion of an esophagus, a portion of a phrenic nerve, and portion of a vascular root.

According to some embodiments, the calculating produces simulated results simulating positions of a catheter used to perform the catheter ablation; and wherein the planned target form is produced based on regions of the target anatomical structure which are accessible by the simulated positions.

According to some embodiments, the simulated positions are constrained by the mechanical properties of the catheter.

According to some embodiments, the simulated positions are constrained by an anchor position applied to a portion of the catheter.

According to some embodiments, the received data comprises 3-D imaging data of the patient-specific anatomy.

There is provided, in accordance with some exemplary embodiments, a system for planning an ablation plan of a target tissue in a patient, the system comprising a processor configured to: calculate simulated results of one or more operations to lesion the target tissue, based on data characterizing patient-specific anatomy comprising at least the target tissue; and produce an ablation plan comprising a set of ablations applied along an extent of the target tissue; wherein the data include data on dielectric properties associated with the target tissue; and wherein the ablation plan is produced based on based on one or more criteria evaluated on the simulated results.

According to some embodiments, the data include data on thermal properties associated with the target tissue.

According to some embodiments, the data characterize geometry of the target anatomical structure, and the ablation plan describes the adjustment of parameters of the ablations as a function of geometry along the planned target form of the lesion.

According to some embodiments, the simulated results comprise thermal simulation of the effect of lesioning on the patient-specific anatomy, based on thermal characteristics associated with the patient-specific anatomy.

According to some embodiments, the simulated results comprise simulation of lesion effects on one or more non-target anatomical structures, and the extent of the set of ablations is adjusted to avoid lesioning of the non-target anatomical structure.

According to some embodiments, the simulated results comprise simulation of lesion effects on one or more non-target anatomical structures, and ablation parameters along the set of ablations are adjusted to avoid lesioning of the non-target anatomical structure.

There is provided, in accordance with some exemplary embodiments, a method for dynamic adjustment of a plan for catheter ablation of anatomical structure in a patient, the method comprising: receiving an ablation plan for producing a target lesion, the ablation plan describing a plurality of planned ablations by an ablation catheter to a target anatomical structure; comparing at least one planned ablation from the plurality of planned ablations to tracking data describing ongoing use of the ablation catheter; and adjusting the ablation plan, based on differences between the at least one planned ablation and the tracking data, wherein the adjusting comprises calculating simulated results of one or more operations to lesion the target anatomical structure, based on data characterizing patient-specific anatomy comprising at least the target anatomical structure.

According to some embodiments, the data characterizing patient-specific anatomy includes data on dielectric properties associated with the target anatomical structure.

According to some embodiments, the data characterizing patient-specific anatomy includes data on thermal properties associated with the target anatomical structure.

According to some embodiments, the plurality of planned ablations is planned as a sequence of ablation catheter activations corresponding to a sequence of position targets.

According to some embodiments, the ablation plan comprises a sequence of ablation parameter sets for activation of the ablation catheter corresponding to the sequence of position targets, and wherein the adjusting comprises adjusting at least one of the ablation parameter sets.

According to some embodiments, the adjusting comprises adjusting the ablation parameters.

According to some embodiments, the differences comprise insufficient nearness of adjacency of lesioning in the tracking data, compared to the ablation plan.

According to some embodiments, sufficient nearness of adjacency comprises a gap between lesions produced at sequential positions which are less than about 1.5 mm.

According to some embodiments, sufficient nearness of adjacency comprises a gap between lesions produced at sequential positions which are less than about 0.3 mm.

According to some embodiments, ablation plan comprises a relative timing of activations of the ablation catheter for lesioning while moving through the sequence of position targets.

According to some embodiments, the differences comprise a delay between ablations, and wherein the adjusting comprises moving a position target closer to a previous position target, to prevent a gap in the lesion.

According to some embodiments, the differences comprise a delay between ablations, and wherein the adjusting comprises increasing at least one of the groups consisting of ablation duration and an ablation power, to prevent a gap in the lesion.

According to some embodiments, the method comprises calculating simulated results in the adjusted plan of one or more operations to lesion the target anatomical structure, and verifying that the simulated results avoid collateral damage to one or more non-target anatomical structures.

According to some embodiments, the simulated results comprise thermal simulation of the effect of lesioning, based on thermal characteristics associated with tissue near the lesioning positions.

According to some embodiments, the simulated results comprise dielectric simulation of the effect of lesioning, based on dielectric properties associated with tissue near the lesioning positions.

There is provided, in accordance with some exemplary embodiments, a system for dynamic adjustment of a plan for catheter ablation of anatomical structure in a patient, the system comprising a processor configured to: receive an ablation plan for producing a target lesion, the ablation plan describing a plurality of planned ablations by an ablation catheter to a target anatomical structure; compare at least one planned ablation from the ablation plan to tracking data describing ongoing use of the ablation catheter; and calculate an adjustment to the ablation plan, based on differences between the at least one planned ablation and the tracking data, wherein the adjusting comprises calculating simulated results of one or more operations to lesion the target anatomical structure, based on data characterizing patient-specific anatomy comprising at least the target anatomical structure.

According to some embodiments, the ablation plan comprises a sequence of ablation parameter sets for activation of the ablation catheter corresponding to a sequence of position targets, and wherein the adjusting comprises adjusting at least one of the ablation parameter sets.

According to some embodiments, the simulated results comprise thermal simulation of the effect of ablation, based on thermal characteristics associated with tissue sites of the plurality of planned ablations.

According to some embodiments, the differences comprise insufficient nearness of adjacency of lesioning in the tracking data, compared to the ablation plan; and wherein the adjusting is selected to prevent a gap in the lesion, and comprises at least one of the group consisting of: moving a position target closer to a previous position target, increasing an ablation duration, and increasing an ablation power.

There is provided, in accordance with some exemplary embodiments, a method for dynamic adjustment of a plan for catheter ablation of anatomical structure in a patient, the method comprising: receiving an ablation plan for producing a target lesion, the ablation plan including sequence of position targets describing lesioning positions of a target anatomical structure; comparing the sequence of position targets to a sequence of tracked positions of an ablation catheter when the ablation catheter is activated for forming a lesion; and adjusting the ablation plan, based on differences between the sequence of position targets and the sequence of tracked positions, wherein adjusting comprising calculating simulated results of one or more operations to lesion the target anatomical structure, based on data characterizing patient-specific anatomical structure comprising at least the target anatomical structure.

There is provided, in accordance with some exemplary embodiments, a method for planning an ablation plan of a target tissue in a patient, the method comprising: receiving data characterizing patient-specific anatomical structure comprising at least the target tissue; wherein the data includes data on dielectric properties associated with the target tissue; calculating simulated results of one or more operations to lesion the target tissue, based on the received data; and producing a planned target form of the lesion; and providing an indication of the planned target form.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/ or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
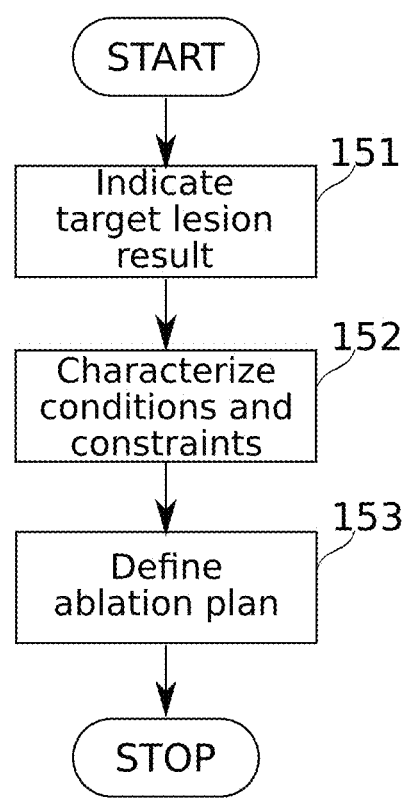
FIG. 1A is a schematic flowchart of a method for planning of an ablation plan, in accordance with some exemplary embodiments of the present disclosure.

The present invention, in some embodiments thereof, relates to systems and methods for treatment with intrabody catheters and, more particularly, but not exclusively, to systems and methods for planning and/or dynamically adjusting planning of treatments such as ablation treatments performed using intrabody catheters.

Overview

An aspect of some embodiments of the current invention relates to systems and methods for planning catheter ablation of a tissue in a patient (producing what is referred to herein as an ablation plan).

In some embodiments, the method comprises receiving (for example, receiving by a lesion planning system, by a processor configured to implement lesion planning, and/or from a user) of an indication of a preliminary target form of a lesion to be formed on and/or within a target anatomical structure of the patient by the planned catheter ablation. Optionally, the preliminary target form is indicated as a path (for example a continuous path, and/or a path described as a series of locations to be lesioned) specified with respect to a representation (e.g., a 3-D display) of patient-specific anatomy.

In some embodiments, the method comprises calculating (e.g., by a lesion planning system) simulated results of lesioning, based on the characterization of data describing patient-specific anatomy. Simulated results may include short-term effects such as heating, collateral effects on nearby tissue, reversible block, and/or edema; as well as predictions of long-term effects such as the irreversibility of block. In some embodiments, the simulation is based on thermal and/or dielectric tissue properties specified in the received data. In some embodiments, the simulation comprises simulation of the effects of power loss density (PLD) in tissue under excitation by a RF field modeled after a field produced by an RF ablation catheter. Optionally, when non-RF ablation is performed (such as by substance injection, cryoablation and/or irreversible electroporation), another equation is used to simulate the initial distribution of ablating energy to (or its ablating removal from) tissue. Additionally or alternatively, simulation of thermal conduction is also performed (for example, based on the thermal continuity equation). Optionally, simulation comprises accounting for interaction between thermal and dielectric properties, for example, changes in dielectric properties during heating as a result of temperature change potentially subsequently influence heating itself in turn. Optionally, simulation comprises accounting for interaction between ablation and physiological responses, for example, edema arising post-ablation potentially affects how later attempts to ablate the same and/or a nearby region proceeds. Optionally, this is accounted for between sequential sub-lesions, and/or as an ablation probe moves along a line of planned ablation.

In some embodiments, the simulated results are used in planning a target form of a lesion (e.g., in planning an ablation_). Optionally, the planning comprises planning a line of planned ablation (e.g., a line of locations at which ablation is performed to create sub-lesions), along which a lesion is to be formed. Optionally, the plan comprises specification of ablation parameters to be used along the line—for example, particular positions, angles, and/or pressures for contact between an ablation probe and target tissue; energies used to activate the probe (optionally including frequency and/or voltage); selection of electrodes (optionally including specification of phased activation of electrodes); and/or durations of ablation. Optionally parameters of ablation (for example, parameters defining energies, details of positioning, and/or durations) are varied at different positions along the line of planned ablation. Optionally, simulation is also used in determining the order of ablations, for example, where ends of a looping line of ablation should meet, and/or placement and/or timing of sub-lesions to take advantage of previously existing lesions and/or recent administration of ablation energy. Herein, the term "sub-lesion" is used to indicate portions of a larger lesion created by an ablation probe upon or along a portion of larger area to be lesioned (e.g., defined as a line or path, but not excluding definitions as areas or volumes). A larger lesion is optionally created by a probe moved stepwise between lesion foci (with ablation at each step defining a sub-lesion), and/or by dragging an ablation probe over a continuous extent of target tissue (where a sub-lesion is defined by the extent of dragged-out ablation, and/or optionally by a change in parameter, for example, a change in ablation power, rate of drag, or another parameter).

In some embodiments, the planning comprises automatic adjustment of the preliminary target form of the lesion to satisfy one or more criteria and/or constraints; for example, criteria and/or constraints affecting safety, procedure outcome, efficiency of power application, and/or treatment duration; and/or practicability of the lesion plan. Optionally, the lesion plan takes into account (and is formulated to avoid damaging) the patient-specific positions of anatomical structures subject to collateral damage (for example, the esophagus, phrenic nerve, and/or venous roots, as in the case of ablations to treat atrial fibrillation). Optionally, the ablation plan takes into account aspects related to maneuvering within the confines of an anatomical space. For example, there may be mechanical limitations on the maneuvering of an ablation catheter. In another example, a requirement for precision of placement may be relaxed in some positions along a line of planned ablation (e.g., a tolerance to gaps in a lesion line may be greater where fibers are oriented so that they are cut by, rather than running between, adjacent sub-lesions); while certain maneuvers (such as joining lesion line ends) are potentially more prone to error and/or complication. In some embodiments, an ablation plan is designed to match more difficult maneuvers to lesion positions where delay and/or error is potentially less damaging to the end result. In some embodiments, the ablation plan is calculated for a shortest line of planned ablation, a minimal number of sub-lesions placed, and/or a minimal use of ablation energy, compatible with the relative importance (e.g., priority and/or weighting) of other criteria and/or constraints.

In some embodiments, the method comprises providing (for example, to a lesion planning system) of an indication of the planned target form. Optionally, the indication comprises showing a line of planned ablation together with a 3-D representation of the target anatomical structure. Optionally, the indication also comprises display of targeted ablation positions along the line, and/or the order and/or timing in which the ablation positions are to be targeted. The indication may also include detailed aspects of the plan such as planned lesion size and/or lesioning parameters such as power and duration.

In some embodiments, an ablation plan includes the definition of intermediate target results which can be monitored while the plan is carried out. For example, properties of a lesion may be monitored during an ablation in progress (for example, based on dielectric property and/or thermal measurements). In some embodiments, intermediate target results are used to adjust one or more parameters of the ablation in progress, and/or another parameter of the ablation plan.

In some embodiments, a preliminary target form is provided automatically and/or by a user as an indication of a selection of a more generally specified lesion form, for example, a selection specified in terms of one or more anatomical landmarks, and/or a topographic relationship of the lesion with respect to the landmarks. For example, the indication may be "surrounding a root of a pulmonary vein" (additionally or alternatively, the root of a plurality of veins, of another blood vessel, or any other relationship between anatomical landmark and lesion form suitable to the application).

In some embodiments, the data characterizing patient-specific anatomy comprise 3-D imaging data (for example, MRI, CT, NMR, and/or data from another imaging modality) describing and/or displaying patient-specific anatomy. In some embodiments, the received data are marked (and/or characterized after receipt) with respect to thermal and/or dielectric properties. Optionally, thermal properties include, for example, thermal conductivity, heat capacity, rate of active heat transfer (for example, by blood perfusion), and/or rate of metabolic heat generation. Optionally, dielectric properties include, for example, the frequency-dependent relative permittivity of tissue, and/or another property related to relative permittivity; for example, as described in the Background of the Invention, herein.

In some embodiments, an ablation plan includes specification of where ablation is to occur; optionally defined as a line or path, an area, and/or a volume (herein, ablation plans for a path are provided as examples, without limitation away from embodiments using areal or volumetric specifications). An ablation plan optionally comprises the definition of ablation parameters along the ablation line (for example, frequency, total energy delivered, power and/or timing). An ablation plan optionally specifies movements of an ablation probe more particularly—for example, from what start point, in what order, to what end point, at what angle, and/or with what timing between movements. Optionally, the plan includes specification of the ablation catheter itself.

An aspect of some embodiments of the current invention relates to systems and/or methods of dynamic adjustment of a plan for catheter ablation of a tissue in a patient. In some embodiments, differences between an ablation plan and the actual ablation as it occurs are automatically adjusted for by changing the plan in media res, optionally while still taking into account criteria and/or constraints affecting safety, procedure outcome, and/or speed and/or practicability of the lesion plan. Plan adjustments may occur entirely automatically, and/or be provided as suggestions and/or alternatives for a user to follow and/or select among. Optionally, alternatives (particularly when they are presented in response in the contingency of a complication or error in the procedure) are presented with an indication of likely relative risks/benefits.

In some embodiments, an ablation plan (for example, an ablation plan as just described) is received; for example, received by a system configured to track an ablation catheter during ablation. In some embodiments, the ablation plan includes a sequence of position targets describing lesioning positions of a target anatomical structure at which sub-lesions and/or other portions of a completed larger lesion are planned to be created. Optionally, the sequence comprises a discrete sequence—for example, a sequence of spot-like sub-lesions along a line of planned ablation. Optionally, the sequence comprises continuous sequence—for example, a sequence of positions passed through as an ablation catheter is dragged along a portion of a line of planned ablation.

In some embodiments, the sequence of position targets is compared to the actual (e.g., tracked by a catheter tracking system) positions of an ablation catheter where it performs ablation. Preferably, the comparison occurs during an ablation procedure. Optionally, this is followed by automatic correction (optionally augmented by user input such as confirmation and/or selection of options) before certain difficulties caused by delay arise—for example, loss of lock between the relative position of the ablation catheter and the lesion, and/or evolution of the lesion to a form which may be more difficult to lesion (tissue typically becomes edematous within a few minutes of lesioning, which can in turn make it difficult to reliably make further lesioning adjustments afterward).

In some embodiments, the ablation plan is adjusted, based on differences between the sequence of position targets and the sequence of tracked positions. Generally, the adjustment seeks to preserve key features of the final lesion which are potentially at risk due to a partial deviation from the plan. One significant form of error which can arise in the treatment of atrial fibrillation by lesioning is the placement of sub-lesions which are not sufficiently close to prevent impulse transmission from crossing between them. In some embodiments, the plan is adjusts by inserting one or more additional lesions, and/or by adding further lesioning energy at one of the sub-lesion positions. At the same time, in some embodiments, safety constraints are also imposed on the plan: for example, to prevent collateral damage to sensitive structures such as the esophagus, venous roots, autonomic ganglia, and/or phrenic nerve.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Method for Planning an Optimal Ablation Line

Reference is now made to FIG. 1A, which is a schematic flowchart of a method for planning an ablation plan (e.g., defining an ablation line which is optimal according to some selected combination of criteria and/or constraints), in accordance with some exemplary embodiments of the invention. In some embodiments, the planning comprises indicating by a user of a target lesion result (at block 151). Optionally or alternatively, the indication is provided at least partially automatically. At block 152, in some embodiments, conditions and constraints which affect how the lesion result is most preferably achieved are characterized, optionally including the use of imaging data defining tissue types and positions, data describing dielectric and/or thermal characteristics of tissue, and/or user input serving as guidance for the choice of specific optimization method.

At block 153, in some embodiments, an ablation plan is defined, based on the indicated target lesion result, the characterized conditions and constraints (and optionally on a selected method and/or selected parameters of how planning is to be performed based on the other inputs).

Optionally, expected results of an ablation plan are presented to a user a priori, for example, as an ablation line indication presented together with a 3-D model of the target tissue, as one or more estimates of time of ablation (partial or overall), as a likelihood of successful treatment, etc. In some embodiments, likelihood of successful treatment is calculated based on success in other patients having similar ablation procedure characteristics.

In some embodiments, an ablation plan includes specification of where ablation is to occur; optionally defined as a line or path, an area, and/or a volume (herein, ablation plans for a path are provided as examples, without limitation away from embodiments using areal or volumetric specifications). An ablation plan optionally comprises the definition of ablation parameters along the ablation line (for example, frequency, total energy delivered, power and/or timing). An ablation plan optionally specifies movements of an ablation probe more particularly—for example, from what start point, in what order, to what end point, at what angle, and/or with what timing between movements. Optionally, plan includes specification of the ablation catheter itself.

In some embodiments, operations of blocks 152 and 153 in particular are carried out by application of a thermal and/or dielectric property simulation of the tissue to be treated. Characteristics of the simulation are described, for example, in relation to FIGS. 10-13B herein.

Figure 1B:
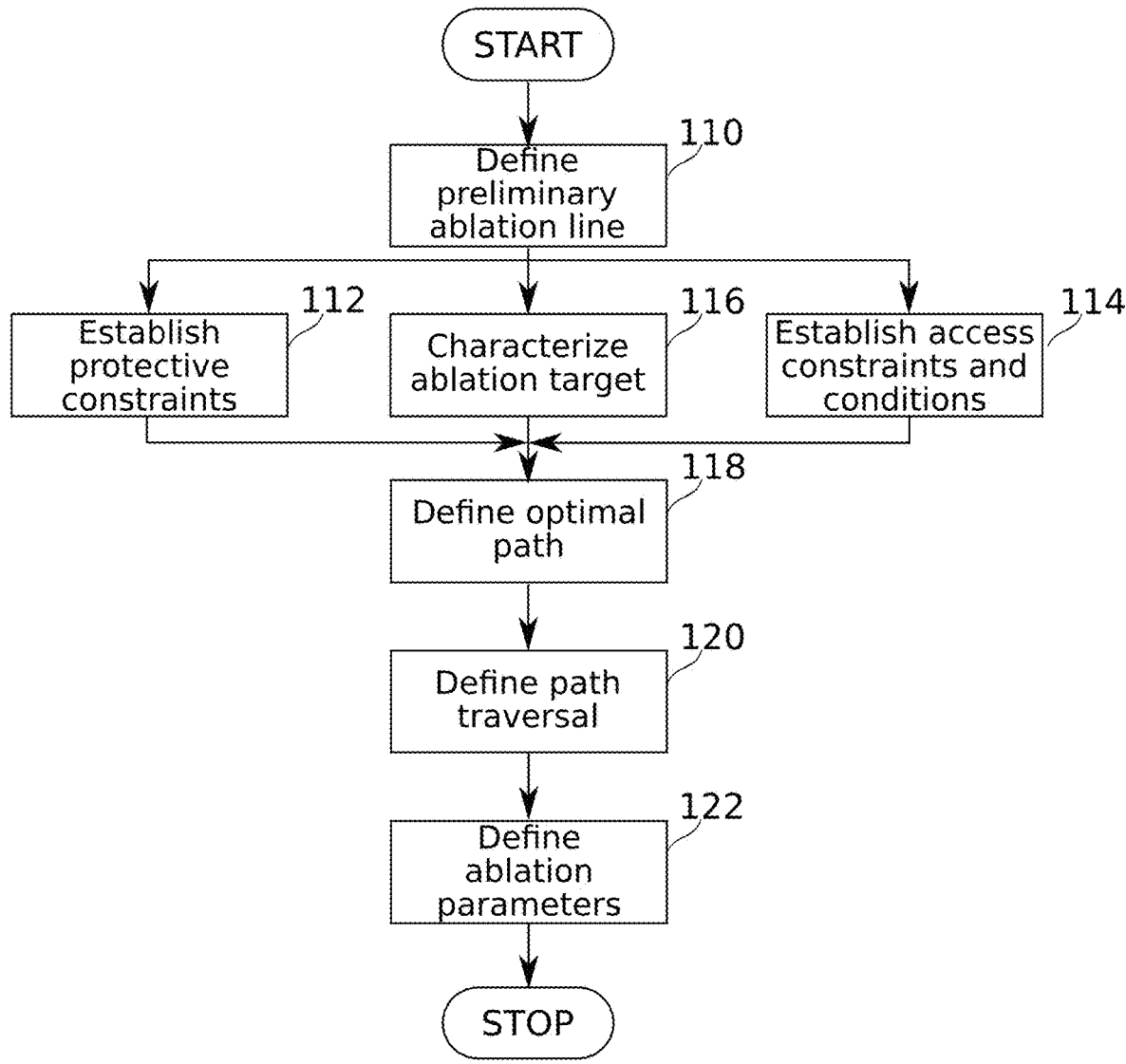
FIG. 1B is a more detailed schematic flowchart of a method for planning of an ablation plan, in accordance with some exemplary embodiments of the present disclosure.

Reference is now made to FIG. 1B, which is a more detailed schematic flowchart of a method for planning of an ablation plan, in accordance with some exemplary embodiments of the invention. The operations referenced by the blocks of FIG. 1B are described in conjunction with interleaved descriptions relating to other figures, for example, FIGS. 9A-9C, 2A-2E, 3A-3C, 4A-4B, and 5A-5B.

Inputs for Planning an Ablation Plan

Treatment by Tissue Lesioning

In some embodiments, ablation treatment of a tissue region such as a tissue wall (for example, cardiac tissue of the atria) comprises the formation of a substantially continuous lesion of tissue which serves as a block to conduction. In some embodiments, the targeted region of block is along a lesion path formed from a plurality of sub-lesions arranged along it a substantially contiguous fashion.

Effective blockage treatment of an irregular impulse conduction disease such as atrial fibrillation potentially fails when the blockage is broken or incomplete. However, the procedure for forming a blocking lesion is subject to conflicting requirements, such as the need to avoid collateral damage to non-target tissue, the difficulty of maneuvering a catheter subject to constrained degrees of freedom, and time pressure to complete the procedure as quickly as possible.

Figure 9A:
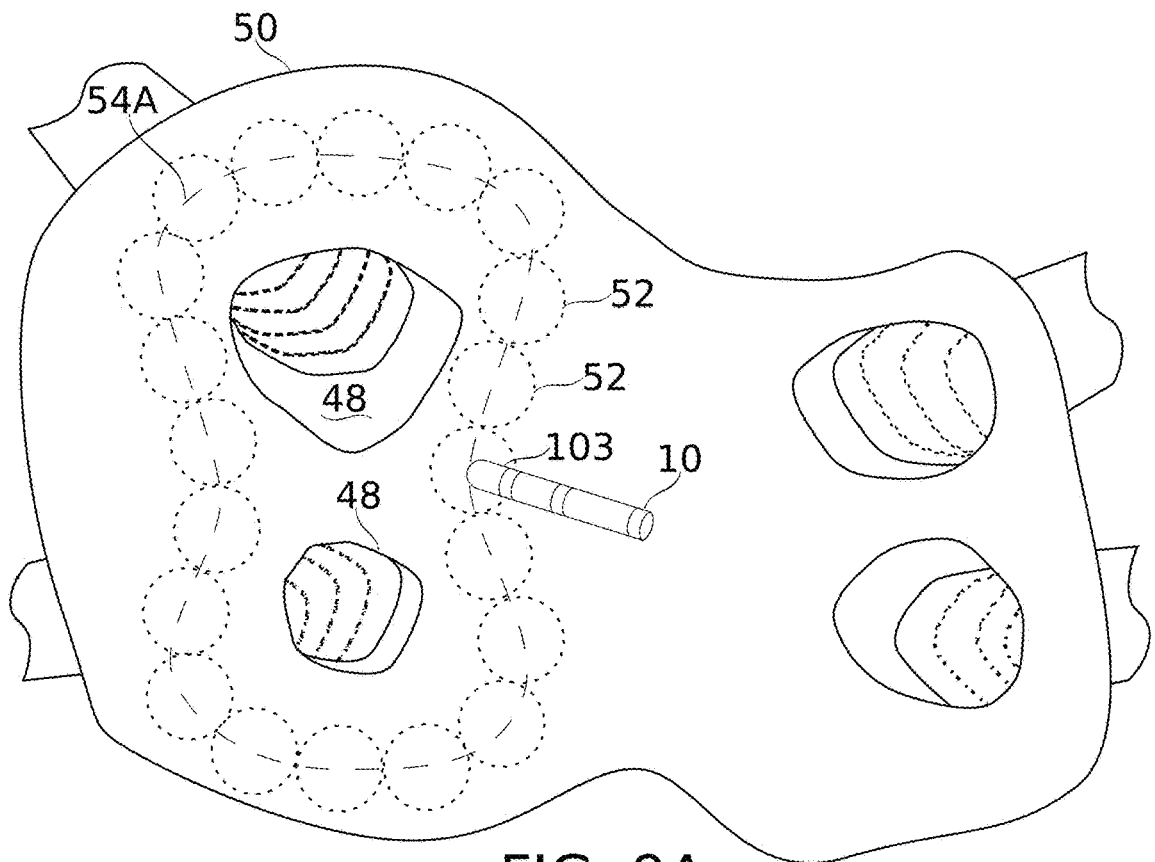
FIGS. 9A, 9B and 9C schematically illustrate aspects of lesioning to block of tissue conduction, for example for the treatment of atrial fibrillation, in accordance with some exemplary embodiments of the disclosure.
Figure 9B:
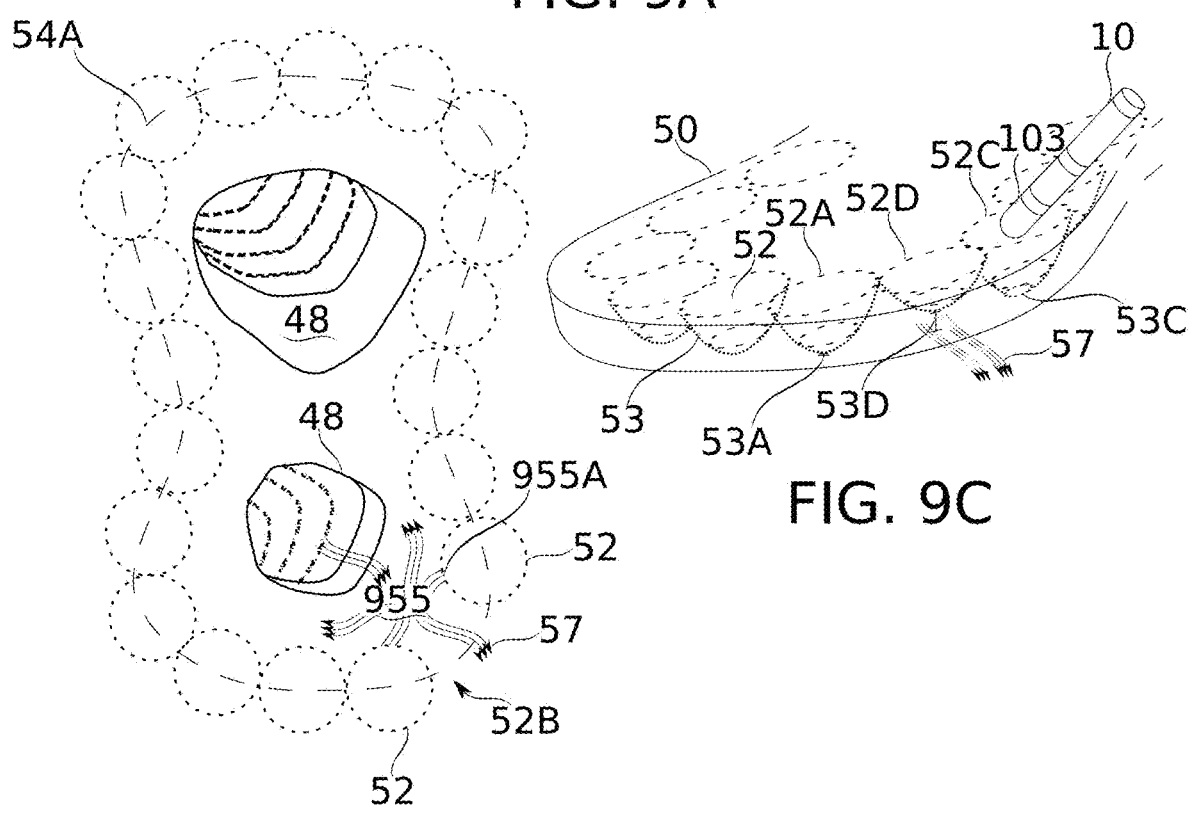
Figure 9C:
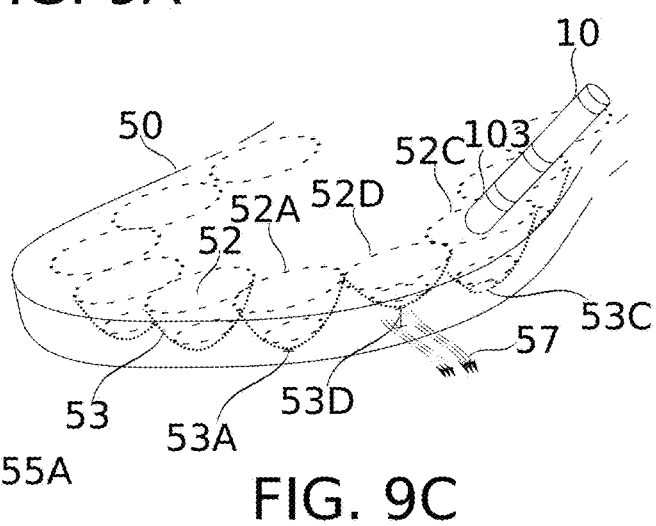

Reference is now made to FIGS. 9A-9C, which schematically illustrate aspects of lesioning to block of tissue conduction, for example for the treatment of atrial fibrillation, according to some exemplary embodiments of the present disclosure. Shown in FIGS. 9A-9B is a lesion path 54A which encircles two pulmonary veins 48 of a left atrium (a view from inside the atrium is shown).

In some embodiments, an ablation probe 10 comprising at least one ablation device 103 is moved sequentially along path 54A, ablating at a plurality of locations to create a chain sub-lesions 52 at each location. In some embodiments, ablation device 103 comprises an electrode, e.g., an electrode used in RF ablation. Optionally, the electrode acts as a sensing electrode for dielectric properties of the tissue near it. Optionally, an additional electrode is provided for sensing dielectric properties.

In FIG. 9B, impulse 955 is shown arising from the vicinity of a pulmonary vein 48. Where it encounters a completed lesion 52 (for example, at boundary 955A), conduction is stopped. However, a gap 52B potentially allows impulse portion 57 to escape into surrounding tissue, where it may contribute to an irregular heartbeat. The minimum size of a gap allowing conduction can be, for example, about 1.0 mm, 1.3 mm, 1.5 mm, or another larger, smaller or intermediate value.

Insofar as lesions may compromise a non-uniform profile through the thickness of a tissue (e.g., as for a hemi-ellipsoid or paraboloid), it should be understood that any region throughout the tissue thickness exceeding this gap width (as long as it has sufficient depth, for example, 0.55 mm, or another value of at least about 0.5 mm-2 mm, to support transmission) can serve as a pathway for impulse "escape". Thus, lesions which superficially contact one another, or even overlap—even if transmural at some region—may nonetheless (at least in principle) be sufficiently distant at some depth to allow impulse escape therebetween. However, for purposes of discussion and illustration, at least partially transmural lesions shown herein as superficially contacting are generally assumed to be close enough to block transmission therebetween at any depth, except as otherwise indicated.

Figure 3A:
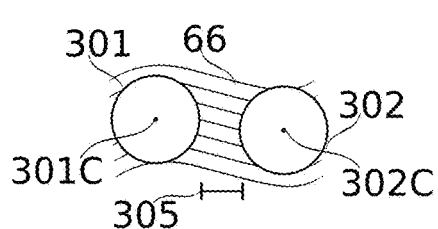
FIGS. 3A-3B schematically illustrate aspects of the planned placement of sub-lesions of a lesion line related to myocardial fiber direction, in accordance with some exemplary embodiments of the present disclosure.
Figure 3B:
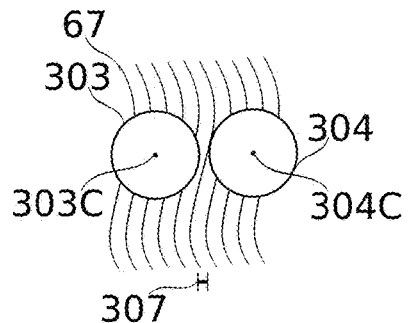

The maximum size of the gap which still prevents blockage may also depend on the structure of the underlying tissue; for example, a direction of myocardial fibers in relation the orientation of the gap (this is also discussed herein, for example, in relation to FIGS. 3A-3B). Optionally, the relevant orientation (which potentially varies through the thickness of the tissue) is selected from one or more layers in which the gap may exist.

FIG. 9C illustrates how lesion depth potentially relates to relatively effective or ineffective conduction block. Tissue region 50 is shown with a chain of lesions 52, 52A, 52D, 52C already formed. The various depths of these lesions are schematically outlined as dotted line paraboloids 53.

Electrode 103 is shown in contact with a surface of tissue 50, over lesion and targeted tissue area 52C. Here, the lesion is transmural, to the degree that it has begun to spread across the opposite surface of tissue 50 at region 53C. Lesion 52A is also a deep lesion, but the degree of transmurality is lower (for example, a small distance 53A has been left). This may not be a reason for concern, if gap 53A is too small to allow impulse conduction. However, at lesion 52D, the lesion is too shallow, and gap 53D is sufficiently large to allow impulse portion 57 to pass through it. In some embodiments, a transmurality gap of about 0.55 mm or smaller is considered small enough to prevent impulse escape, depending also in part on the width of the gap.

Although ablation is generally described herein with respect to ablation of an atrial wall for the treatment of atrial fibrillation, it should be understood that the descriptions also apply, changed as necessary, to the planning of ablation in other tissues; for example: neural tissue, tumor tissue (for example, cancer), other abnormal growth tissue such as warts, skin tissue, mucous membrane, or another tissue.

Preliminary Planning of an Ablation Line

Returning to FIG. 1B: The flowchart begins; and at block 110, in some embodiments, a preliminary line of planned ablation 54 (e.g., lesion path 54A) is defined. The definition is optionally by a user drawing or otherwise indicating a line (for example, on a computerized display of a schematic and/or anatomical representation of the target region). Optionally, the user indicates a preferred preliminary line type (e.g., by selecting from a menu a target such as "around the superior left pulmonary vein root", or another such target). Optionally, a preliminary line of planned ablation 54 is automatically generated and/or selected based on the indication. Optionally, automatic calculation of a final line of planned ablation proceeds directly from the basic indication of an ablation target; for example, based on criteria described in relation to blocks 112, 114, 116.

The line of planned ablation can be defined on any suitable tissue surface; for example, within the left atrium (e.g., around one or more pulmonary veins), or within the right atrium (e.g., around one or more branches of the vena cava). For purposes of discussion, the example of an ablation line in a left atrium is described, however it is to be understood that the discussion also applies, changed as necessary, to the definition of ablation lines along other surfaces.

Figure 2A:
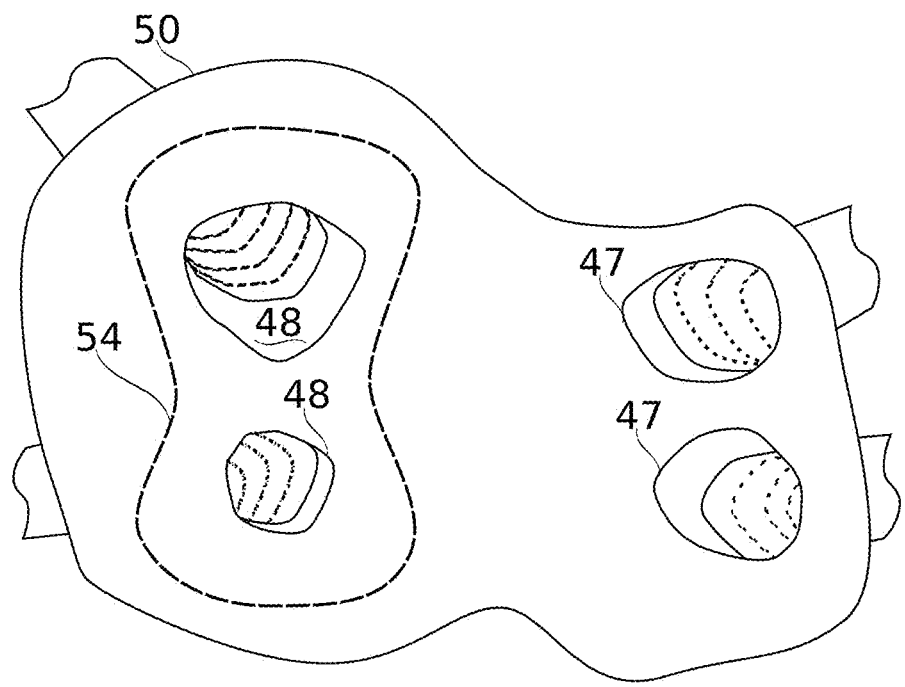
FIG. 2A is a schematic illustration of a tissue wall of a left atrium, including roots of left and right pulmonary veins, and a preliminary line of planned ablation, in accordance with some exemplary embodiments of the present disclosure.

Reference is now made to FIG. 2A, which is a schematic illustration of a tissue wall 50 of a left atrium, including roots of left and right pulmonary veins 47, 48, and a preliminary line of planned ablation 54, in accordance with some exemplary embodiments of the invention.

Optionally, preliminary line of planned ablation 54 encircles both left pulmonary veins, for example as shown. Optionally, for example as discussed with respect to the remainder of FIG. 1B, the line of planned ablation serves as a basis for further modifications which result in a final ablation line which satisfies certain criteria of safety and/or effectiveness. Optionally, as discussed in particular with respect to FIG. 2E, the line of planned ablation is also optimized to a minimal length and/or minimal number of ablation needed to isolate one or more features such as vein roots which preliminary line of planned ablation 54 surrounds, and/or otherwise delineates, indicates, and/or selects.

Returning to FIG. 1B: in some embodiments, based on the preliminary line of planned ablation (or other target definition), further criteria are evaluated for use in the definition of an optimal path of ablation. Optionally, actions of one or more of blocks 112, 114, and 116 are performed in sequence and/or in parallel. These blocks correspond to operations taking place within block 152 of FIG. 1A.

Data for Optimizing an Ablation Line—Protective Constraints

At block 112, in some embodiments, protective constraints are established with respect to the line of planned ablation.

Figure 2B:
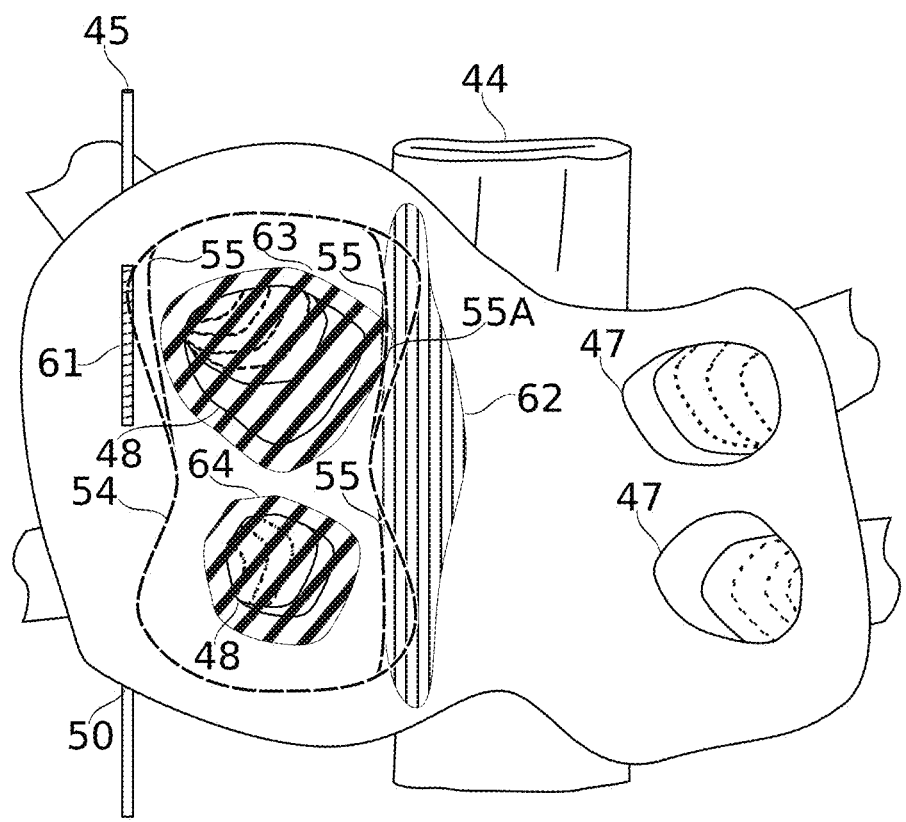
FIG. 2B is schematic illustration of tissue wall, together with a section of a phrenic nerve, an esophagus, and roots of pulmonary veins, each of which is potentially vulnerable to lesion damage due to proximity with tissue wall, in accordance with some exemplary embodiments of the present disclosure.

Reference is now made to FIG. 2B, which is schematic illustration of tissue wall 50, together with a section of a phrenic nerve 45, an esophagus 44, and roots of pulmonary veins 47, 48; potentially vulnerable to lesion-damage around preliminary line of ablation 54 due to proximity with tissue wall 50 at regions 61, 62, 63, or 64; in accordance with some exemplary embodiments of the invention.

In some embodiments, a planned ablation of one tissue (e.g., tissue wall 50) involves potential risk of damage to one or more adjoining tissues. For example, thermal ablation (e.g., by RF energy application) which enters into region 62 of tissue wall 50 potentially also induces heating in esophagus 44 which could lead to damage. Region 61, adjacent to a portion of phrenic nerve 45, is another region of potential risk; damaging the phrenic nerve can lead to partial respiratory paralysis. In some embodiments, lesion placement criteria exclude and/or limit lesioning from entering certain regions of the lesioned surface itself. Regions 63 and 64 are defined, for example, to exclude lesions from entering the ostia of the pulmonary veins.

In some embodiments, thermal simulation of ablation (where ablation is by heating and/or cooling) is used to define adjacency which leads to risk of collateral tissue damage. Thermal simulation is described, for example, in relation to FIGS. 10-13B herein. In some embodiments, simulation is of ablation by another method, for example, electroporation.

In some embodiments, the simulation results are processed to create a definition of regions of tissue wall 50 which are preferably excluded from ablation, and/or preferably ablated only with parameters tuned to reduce a likelihood of collateral damage. Optionally, the region definition is expressed as a region preferably excluded from consideration as central contact points for an ablation probe. For simplicity of illustration, the schematic representation of FIG. 2B may be understood as adopting this type of definition.

Additionally or alternatively, exclusion is otherwise defined. For example, the definition may be such that no heating or cooling of an at-risk tissue can rise above (or fall below) a certain temperature threshold, according to a simulated ablation operation. In some embodiments, the temperature threshold is, for example, about 50° C., 55° C., 58° C., 60° C., 65° C., 70° C., 75° C., or another larger, smaller or intermediate temperature. Optionally, a functional criterion is used: for example, a plan which includes heating for more than T seconds at energy Y by a probe within X mm is preferably excluded. Optionally, values for T, Y and/or X are chosen based on general simulations and/or experimental data, for use as heuristics in the cases of actual patient treatments. For example, T is varied between about 15 seconds to about 45 seconds; Y varies between about 15 W and 30 W, and/or X varies between about 5 mm-10 mm. Use of heuristic criteria has the potential advantage of bypassing at least some of the computational load of an individualized simulation.

Result-focused criteria potentially allows more flexibility in defining an ablation plan than a strict spatial exclusion criterion. For example, lesioning in a risky area is made potentially safer by controlling parameters such as ablation power and/or ablation timing, optionally in addition to controlling the parameter of ablation probe placement. Conversely, there may be regions where the risk of collateral damage is relatively low. For example, relatively low thermal conductivity of adjacent tissue (e.g., air-filled lung tissue) potentially allows more aggressive lesioning of heart wall tissue, which has a potential advantage for speed of lesioning.

Data for Optimizing an Ablation Line—Access Constraints and Conditions

Returning again to FIG. 1B: at block 114, in some embodiments, constraints and conditions relating to spatial access to a lesion line are defined.

Figure 2C:
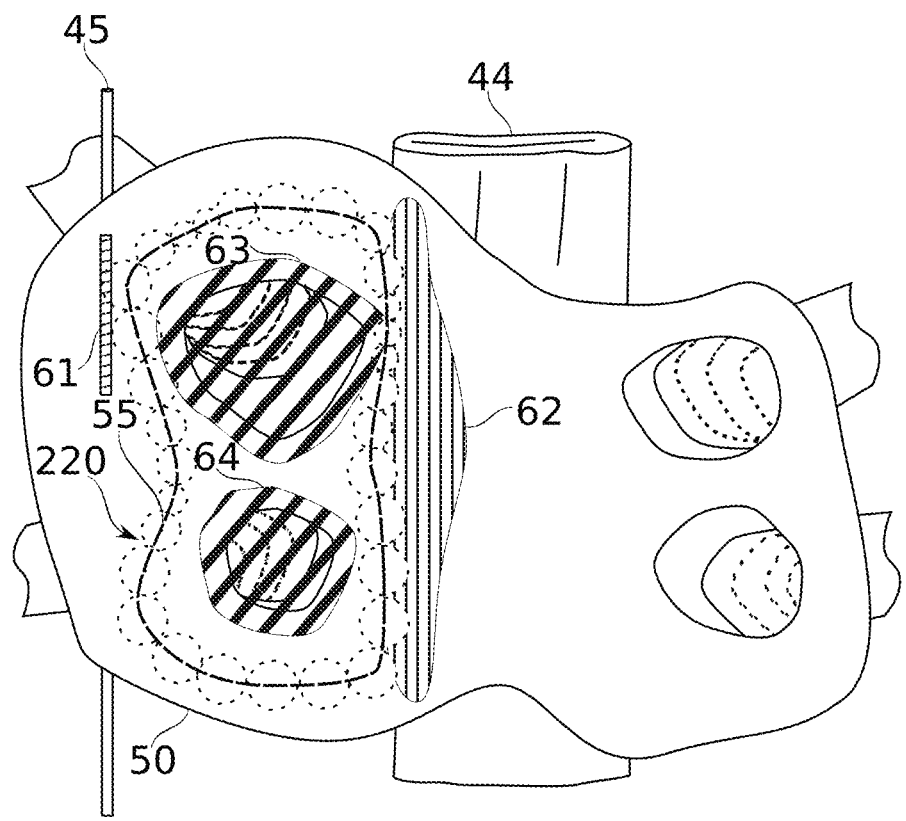
FIG. 2C is a schematic illustration of a planned set of ablation sub-lesions for ablating along line of planned ablation, in accordance with some exemplary embodiments of the present disclosure.
Figure 2D:
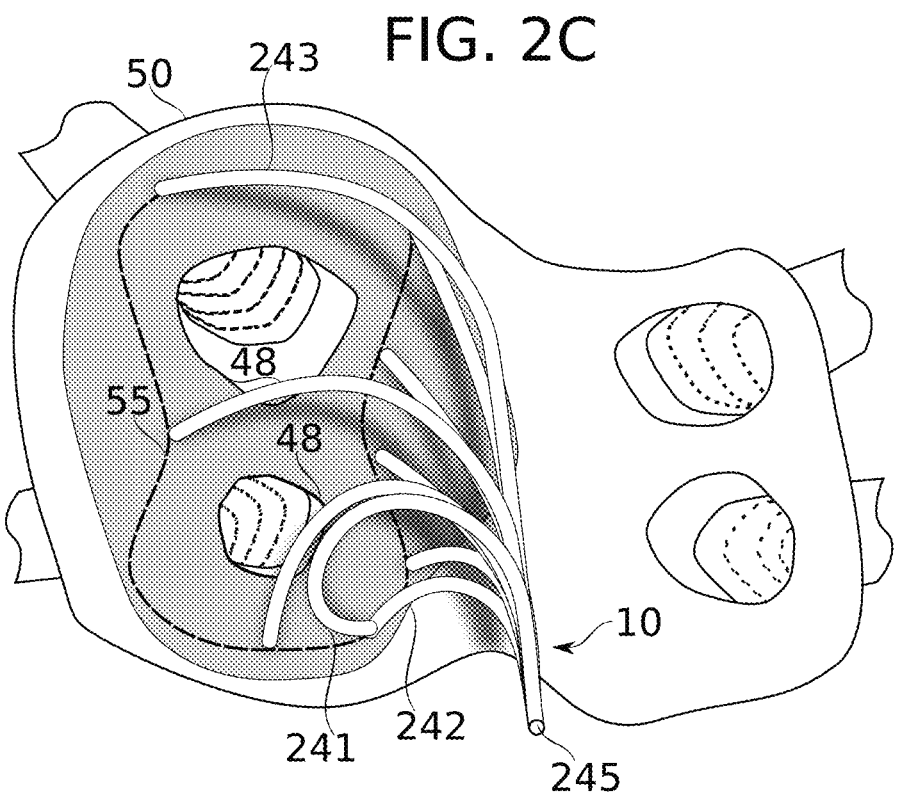
FIG. 2D is a schematic illustration of different positions along planned ablation line reached by respective different positionings of an ablation catheter from a common septal insertion position, in accordance with some exemplary embodiments of the present disclosure.
Figure 2E:
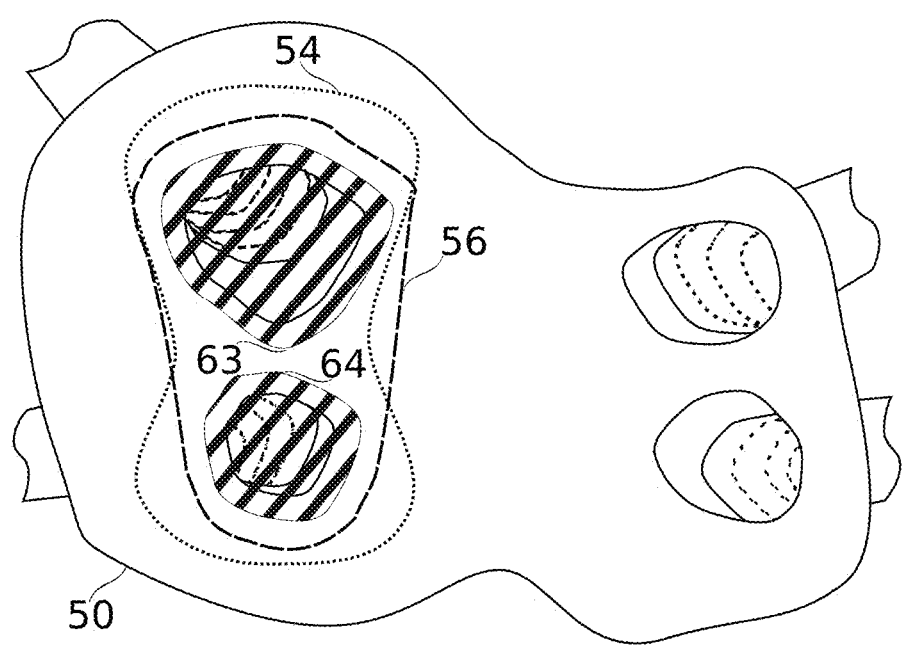
FIG. 2E is a schematic illustration of an alternative line of planned ablation, in accordance with some exemplary embodiments of the present disclosure.

Reference is now made to FIG. 2D, which is a schematic illustration of different positions along planned ablation line 55 reached by respective different positionings 242, 241, 243 of an ablation probe 10 from a common septal insertion position 245, in accordance with some exemplary embodiments of the invention.

In some embodiments, this comprises using a 3-D anatomical model together with a model of the mechanical control characteristics of an ablation probe 10 to calculate which parts of the target region can be physically reached for ablation. In some embodiments, the calculation is additionally constrained, for example, by the location of one or more anticipated access ports 245. For example, an anticipated location of transseptal penetration, and/or the position of a blood vessel used for catheter access are assumed as part of the spatial access definition.

Optionally, the spatial access constraints and conditions include specification of which target surface regions, e.g., of tissue wall 50 can or cannot be reached (optionally, reached from a particular access port 245). In some embodiments, conditions further indicate where access is effectively continuous through some range of ablation probe 10 movements. For example; in FIG. 2D, a potentially continuous sequence of control movements allows ablation along line of planned ablation 55 between position 242 and position 243. However, control movements to allow lesioning in the other direction potentially encounter a discontinuity, e.g., between positions 242 and 241. By "discontinuity" in this context, is meant a condition where an incremental change in the control inputs to ablation probe 10 cannot be used to make a corresponding incremental change in a selected position of ablation along an ablation path (e.g., because ablation probe 10 has reached a limit of movement). However, it may be possible to proceed along the path by resetting the control degrees of freedom to another configuration, introducing thereby "discontinuity" in control movements relative to path position. Use of this information is described, for example, in relation to the definition of a path traversal plan at block 120.

Data for Optimizing an Ablation Line—Target Characteristics

At block 116 of FIG. 1B, in some embodiments, the ablation target itself is characterized with respect to criteria affecting lesion path planning.

Figure 4A:
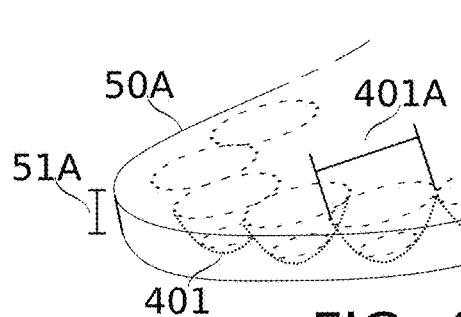
FIGS. 4A-4B schematically illustrate changes in planned lesion extent as a function of tissue thickness, in accordance with some exemplary embodiments of the present disclosure.
Figure 4B:
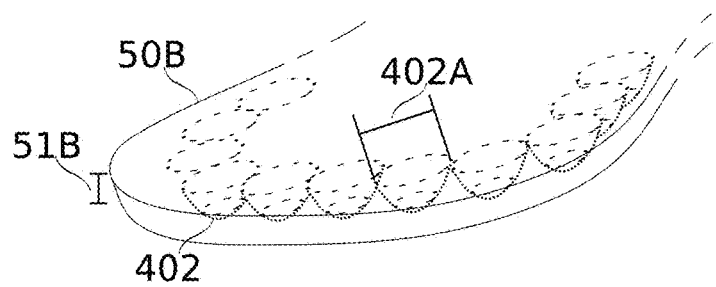

Reference is now made to FIGS. 4A-4B, which schematically illustrate changes in planned lesion extent 401A, 402B of lesions 401, 402, in tissue walls 50A, 50B as a function of tissue thickness 51A, 51B, in accordance with some exemplary embodiments of the invention.

In some embodiments, a goal of ablation is to create a blockage lesion having a substantially transmural extent. To meet this goal, thicker tissue walls potentially require application of more lesioning energy (e.g., at a higher power and/or for a longer time) than thinner walls. Over-lesioning, however, can weaken the tissue, and/or lead to damage to surrounding tissue. Over-lesioning can also extend lesioning time unnecessarily. In some embodiments, tissue thickness throughout the region targeted for lesioning is characterized, for example based on analysis of anatomical images of the individual patient (obtained, e.g., by MRI, CT, or another method), and/or based on tissue atlas information.

Reference is now made to FIGS. 3A-3B, which schematically illustrate aspects of the planned placement of lesions 301, 302, 303, 304 related to myocardial fiber direction, in accordance with some exemplary embodiments of the invention.

In some embodiments, the maximum impulse-blocking distance 305, 307 between two sub-lesions 301, 302, 303, 304 centered on points 301C, 302C, 303C, and 304C, respectively, is predicted in part by the orientation of myocardial fibers 66, 67 in the region of the gap. In general, fibers running parallel to the direction of impulse flow across the gap can transmit impulses through a smaller gap (for example, a gap of no more than about 0.3 mm, 0.4 mm, 0.5 mm, or another distance) than fibers running perpendicular to it (where the maximum size of an inhibiting gap may be, for example, about 1 mm, 1.5 mm, 2 mm, or another distance). Discussion of the influence of fiber orientation and gap size on myocardial fiber impulse transmission is found, for example, in Ranjan et al. (*Gaps in the Ablation Line as a Potential Cause of Recovery From Electrical Isolation and Their Visualization Using MRI*. Circ Arrythm Electrophysiol 2011; 4:279-286). In the computational modeling of Ranjan et al., the reported maximum gap at which conductivity failed was 1.4 mm when fiber direction was perpendicular to the ablation line. When fiber direction was parallel to the ablation line, conductivity failure was reported only up to 0.3 mm gaps. Ranjan et al. suggest that larger gaps which appear to at least initially block conduction in in vivo studies may include tissue with temporarily reduced conductivity which could later recover and resume conduction.

In some embodiments of the invention, myocardial fiber orientation is modeled from anatomical atlas data giving typical orientations, and/or measured for the individual patient using, for example, echocardiography-based shear wave imaging (Lee et al., *Mapping myocardial fiber orientation using echocardiography-based shear wave imaging*. IEEE Trans Med Imaging 2012; 31(3):554-62), Diffusion tensor magnetic resonance imaging (Pashakhanlo et al., *Myofiber Architecture of the Human Atria as Revealed by Submillimeter Diffusion Tensor Imaging*. Circ Arrhythm Electrophysiol. 2016; 9:e004133), or another method.

Other characteristics of the ablation target optionally include, for example, a rate of perfusion (which tends to carry heat away from the tissue being lesioned), a rate of metabolic heat generation, and the tendency of the tissue itself to absorb heat—for example, in the case of RF ablation, this relates to the dielectric properties of the tissue and the frequency of the ablation field. Tissue characteristics relating to modeled thermal properties are also discussed, for example, in relation to FIG. 10.

In some embodiments, already existing lesions (e.g., fibrotic tissue), such as from an earlier ablation procedure, are also taken into account. Optionally, such lesions are identified so that they can be incorporated into a new line of planned ablation. The lesions potentially also have different thermal and/or dielectric characteristics which influence simulation of ablation results.

Production of an Ablation Plan

For purposes of explanation, ablation procedure planning (corresponding, for example, to block 153 of FIG. 1A) is described herein in terms of the placement of the ablation path (block 118), the plan of ablation probe movement along that path (block 120), and finally the parameters of ablation which optionally are selected to vary as the probe moves along the path (block 122). However, it is to be understood that in some embodiments, these plan features are optionally determined together and/or in parallel. For example, which sub-lesion positions are optimal along a portion of the lesion path is potentially influenced by how much and/or with what timing lesioning energy is delivered. In some embodiments, determining a final ablation plan comprises iteratively adjusting these plan features to approach more optimal results, and/or generating a selection of alternative plans from which the most optimal result is chosen. In some embodiments, operations of blocks 118, 120 and 122 in particular are carried out by application of a thermal and/or dielectric property simulation of the tissue to be treated.

Optimization of Ablation Path

At block 118 of FIG. 1B, in some embodiments, an optimal path is generated, based on the preliminary ablation line, and on one or more of the data: providing protective constraints (block 112), characterizing the ablation target (block 116) tissue, and describing access constraints and conditions (block 114).

In some embodiments, the optimal path may be understood as the path which best simultaneously satisfies several, potentially contradictory, constraints and/or criteria. In general, the overall ablation plan preferably seeks effectiveness of the block while protecting against collateral damage, and achieving the greatest speed of lesioning compatible with these two goals. More specifically, the constraints and/or criteria include, for example:

minimization of path length;
minimization of sub-lesion number;
minimization of complexity, required precision, and/or time of catheter maneuvering;
avoidance of collateral damage to non-target tissue;
access to the target, dependent, for example, on anatomy shape and/or catheter mechanics; and/or
features of the target anatomy, for example, tissue wall thickness, existing lesions, and/or fiber direction.

In some embodiments, calculation of these criteria and/or conditions is performed based on the data established and/or characterized in blocks 112, 114, and/or 116. Potentially, these criteria are in at least partial conflict. For example, a more effective block may be achieved by a larger lesion, but a larger lesion in turn may be more likely to cause collateral damage to non-target tissue. In another example, completely avoiding a region where collateral damage is a risk may involve circumvention which produces an impractically long ablation line.

In some embodiments, a lesion planning and/or catheter tracking system 1100 (for example, as described with respect to FIG. 11) is provided with one or more algorithms that take criteria-characterizing input (such as the results of blocks 110, 112, 114, and/or 116) and from it generate an ablation plan comprising a line of planned ablation 55. Optionally, the plan also defines ablation parameters to be applied along the line of planned ablation 55. The one or more algorithms take into account criteria which the inputs have calculated, in order to produce an optimal result under some algorithm-dependent regime of the relative influence of these criteria. Optionally, the relative influence of criteria is adjustable by a user. Additionally or alternatively, there may be several options presented to a user (e.g., corresponding to different algorithms, and/or the same algorithm performed using different parameter settings). Each option is potentially optimal under a different regime of how criteria representing risks and benefits are taken into account in planning. In particular, potentially conflicting criteria may be balanced or reconciled, for example: by weighting, by how an algorithm gates options and/or orders calculations considering each criterion, or by another method. Optionally, the user selects and/or modifies the method used to balance and/or reconcile potentially conflicting criteria, e.g., using a computer's user interface.

Moreover, there is optionally a balance kept between any of these criteria (particularly speed) and user intent. For example, a user may propose a preliminary line of planned ablation which is not optimal for minimal length, but which increases a user-perceived margin of error and/or user comfort for lesion placement. Optionally, optimization of the line of planned ablation is performed for criteria of safety and block, while optimization for speed is limited to parameters which do not further adjust the position of the line of planned ablation. Optionally, a user may choose to ablate along a line which follows, or is otherwise placed according to consideration of at least portions of an existing lesion.

With respect to speed of ablation: all things being equal, it is optionally preferable between two alternatives for the line of planned ablation to be shorter, for the number of lesions created to be fewer, and/or for the total energy delivered to be lessened. These criteria of "least ablation" are themselves potentially in partial conflict between each other; e.g., if ablation plan results in fewer but larger ablations, this is a potential advantage for reducing a risk of accidentally leaving an impulse transmission gap, even if there is a corresponding potential disadvantage in terms of time or energy required to create larger lesions. In some embodiments, the optimal tradeoff used in calculation is predetermined. Optionally, however, a user is permitted (e.g., by use of a suitable user interface) to select a relative balance of how conflicting criteria are resolved.

The line of planned ablation 55 shown in FIG. 2B is minimally disturbed from the preliminary line of planned ablation 54 for applying protective criteria, without also minimizing path length. However, reference is now made to FIG. 2E, which is a schematic illustration of an alternative line of planned ablation 56, in accordance with some exemplary embodiments of the invention. In this instance, preliminary line of planned ablation 54 is shown aggressively optimized for reduced length as alternative line of planned ablation 56. Optionally, preliminary line of planned ablation 54 is "shrunk" until some sub-lesions produced therealong would just reach to the limit of vein ostium protection regions 63, 64. In some embodiments, lengthening the path by over-shrinkage is prevented; the effect is as though a rubber band were extended between sub-lesioning which are not in direct contact with the vein ostium protection regions 63, 64.

As for the protective criteria of block 112: in FIG. 2B, line of planned ablation 55 is shown adjusted from preliminary line of planned ablation 54 by diversions which pull the line centrally away from regions 61 and 62 at which ablation is indicated to accompany a potential risk for collateral damage.

Optionally, protective constraints are treated as dominant where they come into conflict with the optimization of procedure speed. For example, satisfying protective criteria of block 112 optionally comprises slowing a rate of ablation, and/or lengthening the line of planned ablation to avoid zones of preferable ablation exclusion. For example, if a preferred set of ablation parameters (e.g., a set which is optimal for speed and transmurality as a function of tissue wall thickness) happens to violate protective constraints, then the line of planned ablation is optionally moved to an area where the protective constraints are satisfied. Additionally or alternatively, the plan is adjusted to reduce ablation "intensity" (e.g., reduced duration, frequency, and/or power) to reduce collateral damage. For example, along a portion of line of planned ablation 55 (within overlap region 55A), vein ostium protection region 63 slightly overlaps with trachea protection region 62. This leaves no apparent unimpeded path for lesioning, but routing ablation around this block would significantly increase the overall length of the lesion line. Reducing ablation intensity through this region is an optional way to keep the line short, while mitigating the potential for collateral tissue damage.

In some embodiments, the access constraints of block 114 establish zones of preferable exclusion for the line of planned ablation. For example, if an ablation probe cannot mechanically reach a surface region from an assumed base position such as a transseptal entry point, then the line of planned ablation is optionally adjusted to avoid it. Alternatively, the plan may be adjusted for use of an ablation probe with different mechanical characteristics, different electrode positions, and/or a different base position.

Planning of Ablation Path Traversal

At block 120 of FIG. 1B, in some embodiments, a traversal plan of line of planned ablation is defined. Optionally, the traversal plan takes into account mechanical and/or spatial limitations of the positioning of the ablation probe. Optionally, the traversal plan is designed so that positioning operations which entail the greatest risk of placement error and/or delay occur at positions where larger gaps between lesions are potentially least likely to enable impulse propagation therethrough.

Figure 3C:
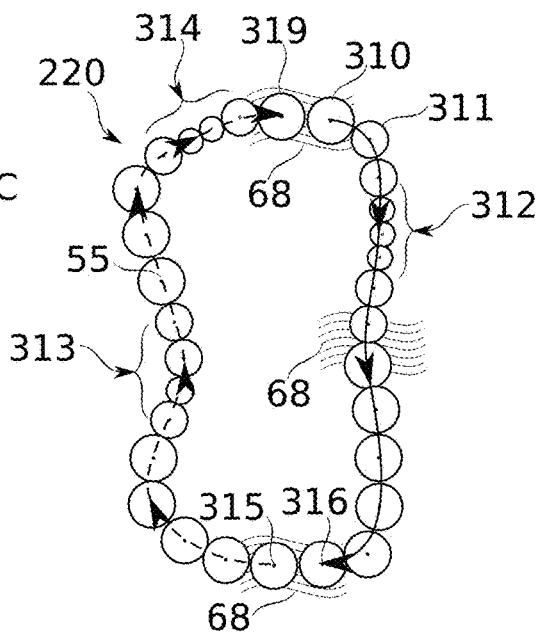
FIG. 3C is a schematic illustration highlighting details of a planned set of sub-lesions of a lesion line, and their traversal along a line of planned ablation, in accordance with some exemplary embodiments of the present disclosure.

Reference is now made to FIG. 3C, which is a schematic illustration highlighting details of a planned set of ablations creating sub-ablations 220 and their traversal along a line of planned ablation 55, in accordance with some exemplary embodiments of the invention.

Potentially, positioning for lesioning achieved by direct movement between adjacent lesion foci (sub-lesions, for example) is less prone to errors and/or delays which can introduce gaps in the ablation line that permit impulse transmission. However, joining between the starting and stopping points of a lesion traversal line generally requires making a join between sub-lesions where the later sub-lesion is formed up to several minutes after the earlier one. During the interval, not only does the tissue tend to cool (which can reduce a degree of sub-lesion chaining described in relation to FIGS. 5A-5B), but there can also be an edematous response by the tissue which affects ablation effectiveness. In some embodiments, these effects are simulated as part of ablation planning.

In some embodiments, a traversal plan is designed so that such joins are positioned over regions where myocardial fiber orientation 68 (just a few patches of fiber orientation 68 are shown for illustration) generally cuts across to the direction of potential propagation across the gap (fiber orientation is also discussed in relation to target characterization at block 116, and with respect to FIGS. 3A-3B herein). For example, sub-lesion 310 is optionally a preferred candidate for a starting lesioning position, since the local direction of fibers means that sub-lesion neighbor 319 can be placed with greater error, while still maintaining an effective block.

Another instance where repositioning is optionally planned for is at places where the ablation probe reaches the end of its available travel, and must be reconfigured in order to continue along the path. An example of two different catheter configurations reaching the same region is shown, for example, at positions 242 and 241 of ablation probe 10 in FIG. 2D, corresponding to sub-lesions 316 and 315 of FIG. 3C. In some embodiments, where there is some overlap of the zones of travel of the two configurations, the break point is chosen for ease of joining up the two different lines. For example, advantage is taken of the reduced constraint on positioning represented by myocardial fiber orientation at some positions.

Planning of Sub-Lesions

At block 122 of FIG. 1B, in some embodiments, ablation parameters are defined for sub-lesion positions along the line of planned ablation 55. Circumstances affecting planned ablation parameters include the thickness of tissue, which may vary along the extent of the line of planned ablation 55, the proximity of tissue prone to collateral damage (particularly the phrenic nerve 45 and the esophagus 44), the proximity of tissue which is relatively resistant to heat damage (e.g., relatively non-heat-conductive lung tissue), the predicted relative timing of lesion placements (which may be keyed, for example, to activation of the ablation catheter for lesioning), and other thermal parameters associated with a thermal simulation of ablation, for example as described in relation to FIGS. 10-13B.

Continuing reference is made to FIG. 3C. Reference is also made to FIG. 2C, which is a schematic illustration in a wider anatomical context of the planned set of ablation sub-lesions 220 for ablating along line of planned ablation 55, in accordance with some exemplary embodiments of the invention.

It is noted that most of the sub-lesion locations marked (e.g., sub-lesion 310) are relative large in diameter. Optionally, this reflects a default ablation setting, wherein a full-power, full-duration ablation is planned to be carried out at the given position. This may be appropriate, for example, when the tissue wall 50 is relatively thick, and there is a relatively low risk of serious collateral damage which allows proceeding rapidly. Somewhat smaller sub-lesion sizes are shown, for example, at sub-lesion 311, and in particular through regions 312, 313, and 314. In some embodiments, smaller sub-lesions are formed, for example, by use of a lower ablation power, and/or by use of a shorter lesioning dwell time. Smaller lesions through region 312, for example, optionally reflect an increase in care to avoid damage to the esophagus (compare, for example, to the positions of ablation sub-lesions 220 in FIG. 2C relative to regions 62 and 63). Optionally, smaller lesions through regions 313 and 314 reflect the presence of another constraint or condition; for example, a thinner tissue wall thickness, and/or a locally higher rate of perfusion which reduces the ability to heat nearby tissue.

Figure 13A:
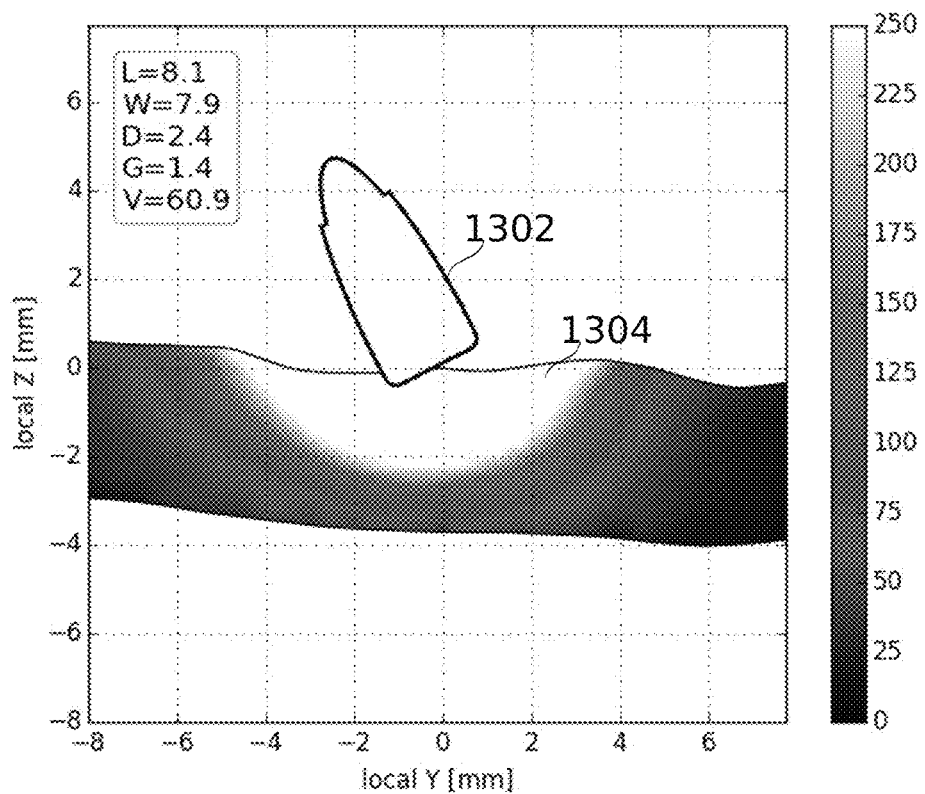
FIG. 13A is a graph depicting the calculated PLD pattern created by an electrode (e.g., RF ablation electrode(s)) in a tissue, in accordance with some embodiments of the present disclosure.
Figure 13B:
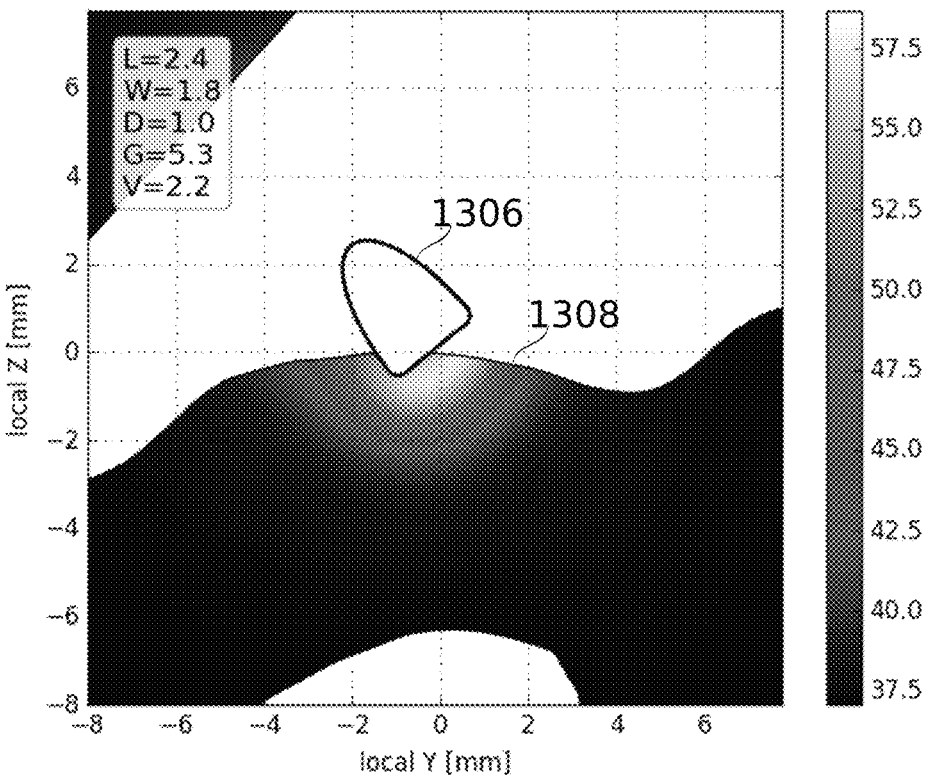
FIG. 13B is a graph depicting the calculated temperature pattern (in degrees Celsius) created by an electrode (e.g., RF ablation electrode(s)) in a tissue, in accordance with some embodiments of the present disclosure.

Although sub-lesions 220 are drawn as abutting circles, it is to be understood that an ablation plan optionally overlaps sub-lesion areas to help ensure that deeper tissue is not subject to impulse-transmitting gaps. Optionally, sub-lesion shapes are different than circular, due, for example, to oblique angles of contact between the ablation probe 10 and the tissue wall (an example of this is shown in FIGS. 13A-13B). Optionally, an ablation probe is slowly dragged across a surface, leaving a more streak-like sub-lesion. Another factor which can affect sub-lesion shape is the interaction between heating delivered at different sub-lesion locations.

Figure 5A:
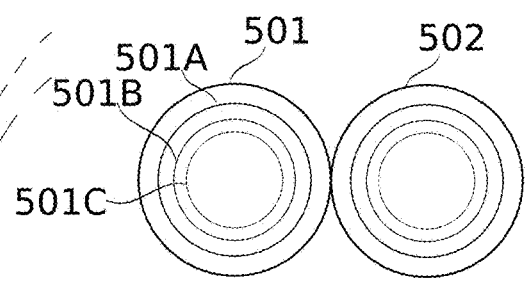
FIGS. 5A-5B schematically illustrate planning for adjacency effects of tissue lesions made in two different sequences, in accordance with some exemplary embodiments of the present disclosure.
Figure 5B:
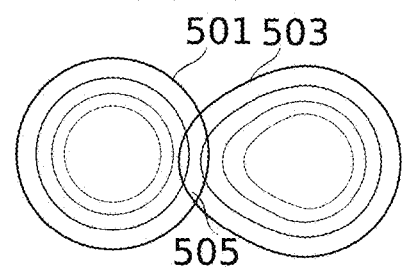

Reference is now made to FIGS. 5A-5B, which schematically illustrate planning for adjacency effects of tissue lesions 501, 502, 503 made in two different sequences, in accordance with some exemplary embodiments of the invention.

A superficial extent of sub-lesion 501 is represented by the outer circle, while progressively smaller interior circles 501A, 501B, 501C represent lesion extent at gradually increasing depths (depth is similarly represented for sub-lesions 502 and 503). In some embodiments, after a first lesion 501 is made, a second lesion 502 is made only after the elapse of a cool-down period. Then the two lesions potentially are made as if independent from one another. Unless care is taken to ensure sufficient overlap, this can increase the potential for an impulse-permissive gap, particularly in the deeper layers.

In FIG. 5B, however, sub-lesion 503 is placed almost immediately after creation of lesion 501, while there remains some residual heating from the previous ablation. In this case, thermal simulation may show that the two sub-lesions will tend to merge, for example as shown at region 505. In some embodiments, an ablation plan reflects assumptions about how quickly heating at each planned position for creating a sub-lesion can begin (optionally, it begins effectively immediately when a dragging technique is used). This provides potential advantages both for creating gap-free transmural lesions, and for increasing the speed with which lesions can be formed.

Optionally, the ablation effect of a first sub-lesion may be simulated as well. For example, residual heating and/or lesioning effects on tissue parameters are optionally inputs to a simulation of a second sub-lesion ablation (for example, one made in tissue sufficiently near to the first sub-lesion to be potentially affected). Optionally, such simulation facilitates defining the sub-lesioning sequence; e.g., the order and/or timing by which sub-lesions are ablated.

Figure 7A:
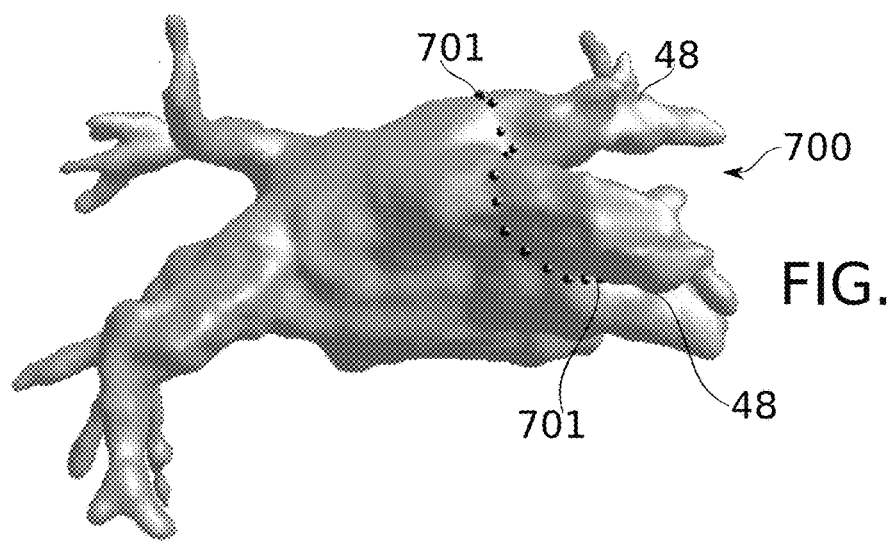
FIGS. 7A, 7B and 7C illustrate the 3-D display of a lesion plan for a left atrium, in accordance with some exemplary embodiments of the present disclosure.
Figure 7B:
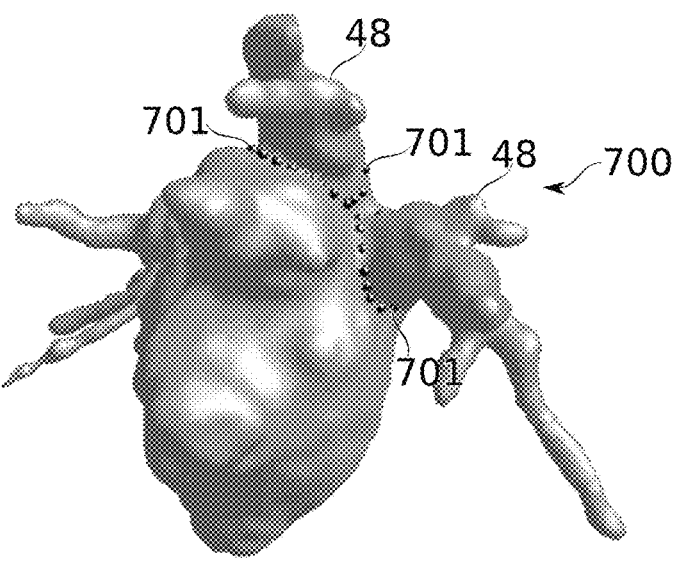
Figure 7C:
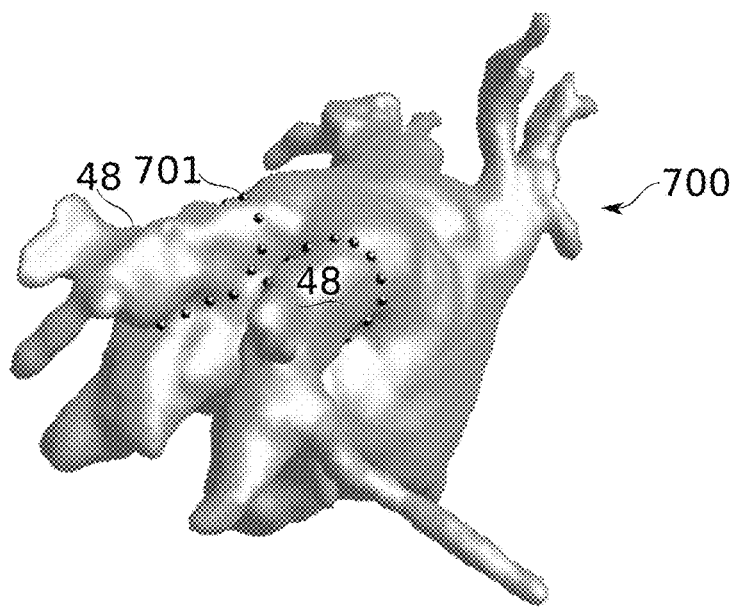

Reference is now made to FIGS. 7A-7C, which illustrate the 3-D display of a lesion plan for a left atrium 700, in accordance with some exemplary embodiments of the invention.

In some embodiments, the results of lesion planning are shown to a user by use of a 3-D display. FIGS. 7A-7C illustrate one such plan display. A 3-D model of a left atrium 700 (porcine, in this example) is shown from three viewpoints. Sub-lesion loci are indicated by the trails of dark marks 701 (modeled as embedded spheres, for example). In this case, the lesion lines are shown extending around portions of the roots of the inferior vena cava 48.

Application and Dynamic Adaptation of an Ablation Plan

Figure 6:
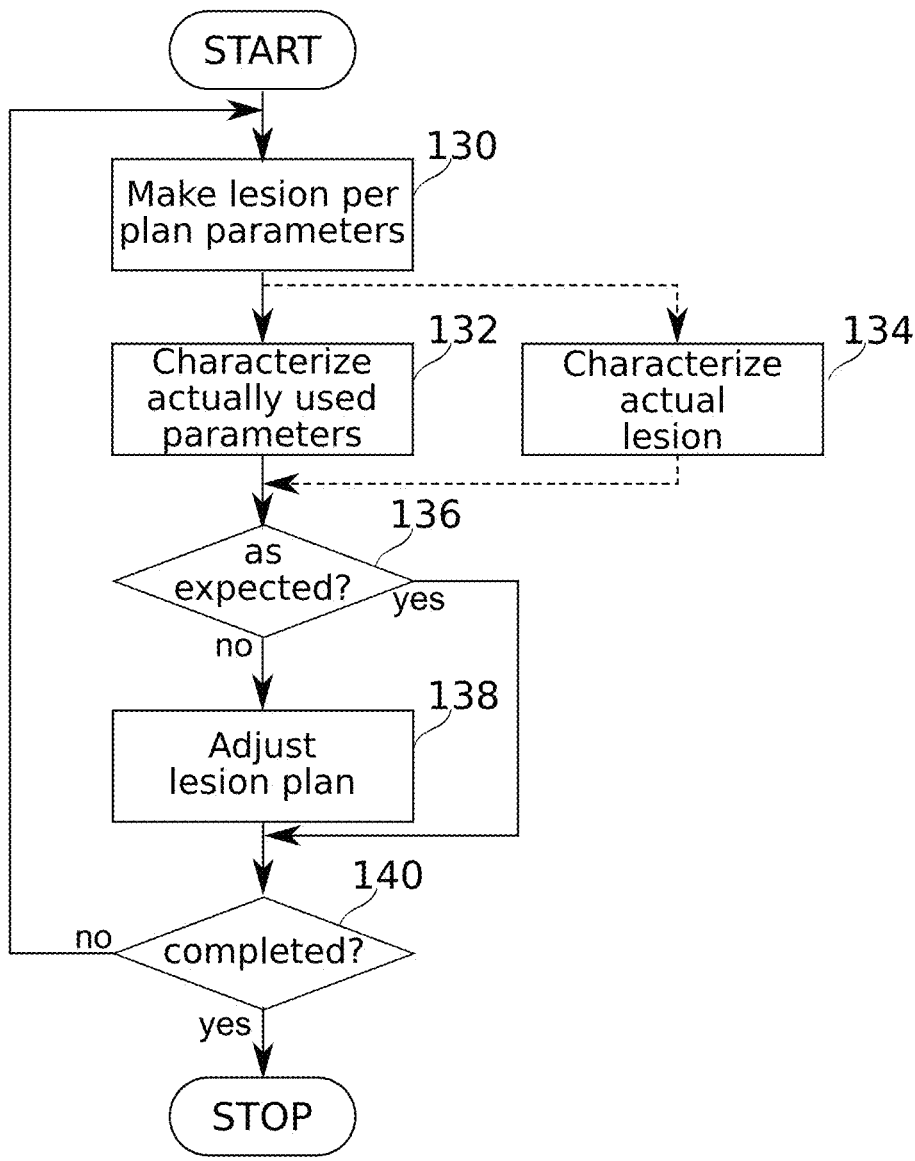
FIG. 6 schematically illustrates a method of real-time use of an ablation plan with optional adjustment, in accordance with some exemplary embodiments of the present disclosure.
Figure 8A:
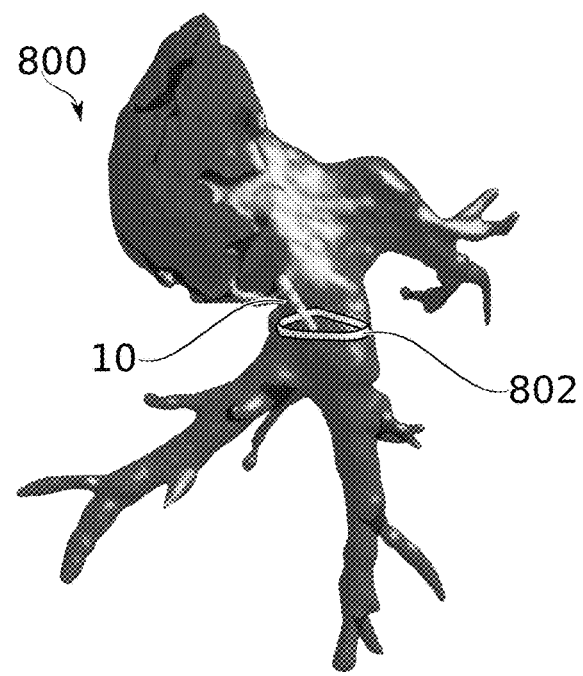
FIG. 8A illustrates the 3-D display of a planned lesion ablation line for a left atrium, along with an ablation probe, in accordance with some exemplary embodiments of the present disclosure.
Figure 8B:
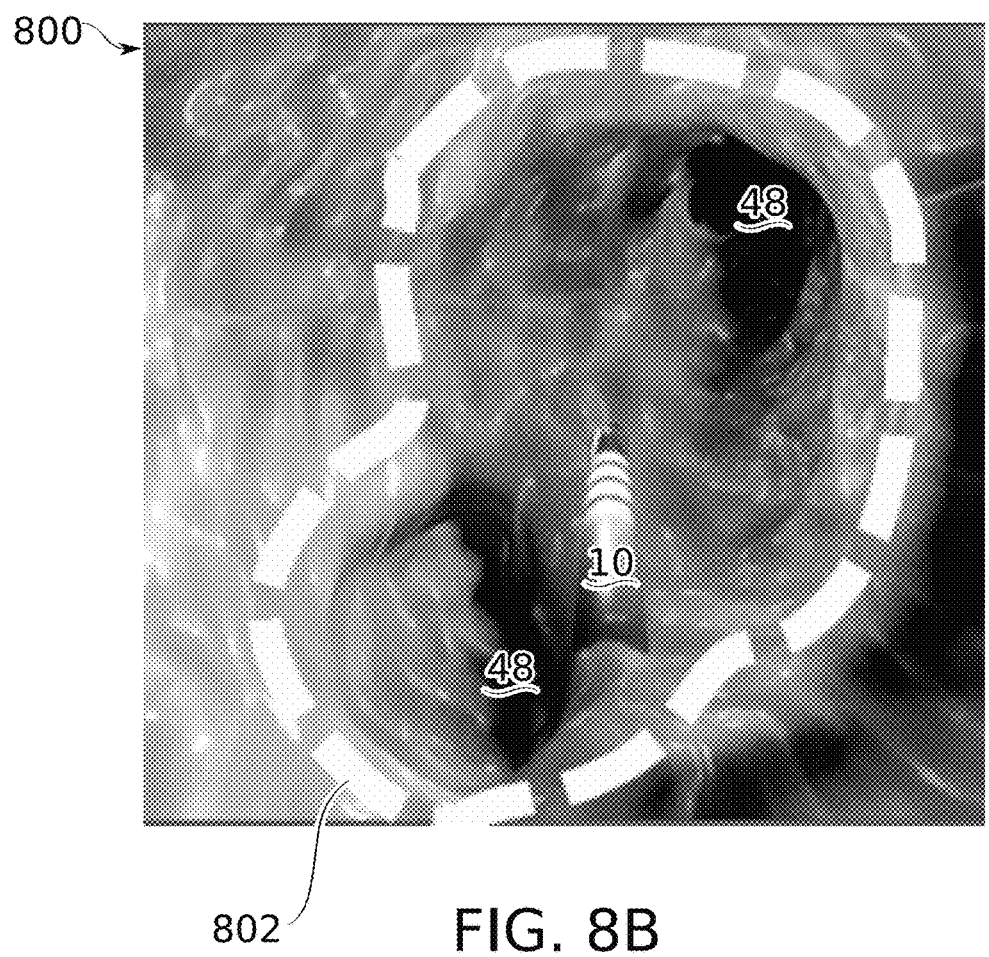
FIG. 8B illustrates an interior-D view of left atrium, probe, and planned ablation line, in accordance with some exemplary embodiments of the present disclosure.

Reference is now made to FIG. 6, which schematically illustrates a method of real-time use, with optional adjustment, of an ablation plan, in accordance with some exemplary embodiments of the invention. Reference is also made to FIG. 8A, which illustrates the 3-D display of a planned lesion ablation line for a left atrium 800, along with an ablation probe 10, in accordance with some exemplary embodiments of the invention. Reference is further made to FIG. 8B, which illustrates an interior 3-D view of left atrium 800, probe 10, and planned ablation line 802, in accordance with some exemplary embodiments of the invention.

In some embodiments, a line of planned ablation 802, together with parameters of planned sub-lesions 220 is used during a procedure by combining measured ablation probe positions within the body with cues to guide operation of the ablation probe so that the previously determined ablation plan is followed.

The flowchart begins (after production of an ablation plan, for example by the methods of FIGS. 1A and/or 1B), and at block 130, in some embodiments, a portion of a planned lesion is made (e.g., a sub-lesion comprising ablation from a fixed ablation probe location, or a dragged-out portion of a lesion). Optionally, the lesion is made in conjunction with visual guidance provided to the user, for example, visual guidance as shown in FIGS. 8A-8B. In FIG. 8A, visual guidance is presented from an outside-the-heart point of view. In FIG. 8B, the point of view is that of the ablation catheter itself, shown as if from within a heart chamber emptied of blood. Optionally, as the actual ablation probe is moved, its motions (measured, for example, by system 1100 of FIG. 11) are shown also in a live presentation of the views of FIG. 8A and/or FIG. 8B. In some embodiments, the display is adjusted to also include anatomically realistic tissue coloring and/or responsiveness to ablation probe contact and/or to the effects of ablation itself.

Optionally, selection of pre-planned ablation parameters is automatically made when an ablation probe approaches the next planned lesion position. Optionally, the system guides the user to the next planned lesion position. Optionally, a user is provided with an interface which allows modifying or overriding these settings.

In some embodiments, the system adapts the ablation plan to actual events during ablation, for example, as now described in relation to blocks 132, 134, 136, 138, and 140.

At block 132, in some embodiments, the system 1100 characterizes parameters such as ablation probe position and settings of the actual ablation operation performed (optionally, the ablation operation set to be performed based on the current ablation probe position and settings). Optionally, information about the ablation probe position includes a contact force or other assessment of contact quality (e.g. dielectric property contact quality assessment) between the ablation probe and target tissue. Optionally, the new state of tissue in the lesioned region is modeled, based on actual ablation position and parameters, and on data previously configured for thermal simulation. Additionally or alternatively, at block 134, in some embodiments, the lesion actually created is itself characterized, for example, by the analysis of dielectric measurements and/or temperature readings.

At block 136, in some embodiments, a determination is made as to whether or not the plan is still being followed as currently defined. If so, flow continues at block 140.

Otherwise, at block 138, in some embodiments, the lesion plan is adjusted. Adjustment may be made in any parameter of the lesion plan to adjust, for example: to a deviation from the previously planned timing and/or placement of sub-lesions, to a deviation from an expected effect of a lesioning operation (as measured, for example, from dielectric measurements of lesion extent), and/or for a deviation from an expected pre-lesion tissue state (for example, an expected pre-existing lesion is found to be of a different extent; measured, for example, by dielectric measurements and/or measurements to assess functional blockage of impulse transmission).

For example, if a sub-lesion was placed with too large a gap between it and an adjacent sub-region, the plan may be adjusted to fill in the gap region. In another example, if more time has passed between sub-lesions than the current plan anticipates (such that there has been too much cooling in the interim), the recommended placement of the next sub-lesion is brought closer to the previous lesion.

The lesion plan is optionally be adjusted in accordance with any of the methods described in FIG. 1A or 1B. The actual measured parameters (e.g., as measured in blocks 132 or 134) are optionally inputted to the simulation in order to adjust the lesion plan.

At block 140, in some embodiments, a determination is made as to whether or not the lesion plan has been adequately completed (e.g., according to completion of the planned sequence of steps, and/or based on verification measurements of the actual lesion). If not, the flowchart returns to block 130. Otherwise, the flowchart ends.

Systems and Methods for Thermal Simulation of Tissue Ablation

Figure 10:
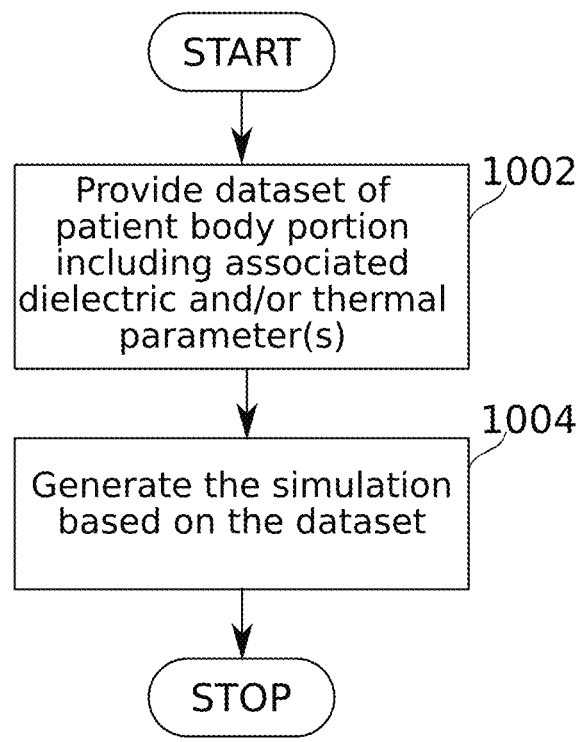
FIG. 10 is a schematic flowchart of a method for generating a tissue simulation including thermal and dielectric properties, in accordance with some embodiments of the present disclosure.

Reference is now made to FIG. 10, which is a schematic flowchart of a method for generating a tissue simulation including thermal and dielectric properties, in accordance with some embodiments of the present invention. Concurrent reference is also made to FIG. 11, which is a block diagram of components of a system for tracking the position of an intra-body catheter, which is also optionally configured as a system for lesion planning, in accordance with some embodiments of the present invention.

In some embodiments, the method receives a dataset representing an anatomical image (e.g., 3-D CT images) of the patient, and based on dielectric properties of tissue types (e.g., impedance and/or conductivity) and/or thermal properties (e.g., thermal conductivity, heat capacity, and metabolic heat generation) identified within the anatomical image, creates a dielectric map and/or a thermal map (i.e., dataset) for the patient. The dielectric and/or thermal map is used as a basis for a generating a simulation of lesioning along a line of planned ablation during a simulated procedure. The output of the simulation is used to predict ablation procedure effects on actual tissue; for example, ablation using an RF ablation catheter.

In some embodiments, modeled thermal parameters include thermal properties general to animate or inanimate matter, for example, thermal conductivity and/or heat capacity; and/or thermal properties specific to biological tissues, for example, metabolic heat generation, absorption rate, and/or blood perfusion rate. Optionally, the thermal properties are used as inputs into a bio heat formulation of a heat equation to estimate temperature evolution in the region of interest as a function of time and/or space.

In some embodiments, electric and/or dielectric parameter values are associated with the thermal parameter values. Optionally, the electric and/or dielectric properties are temperature and/or frequency dependent. Optionally, estimation of the dielectric parameter values includes simulating temperature-dependent dielectric parameter effects of the thermal parameters, and/or measuring and/or calculating the thermal parameters in real time.

Other inputs to the simulation optionally include data about the ablation probe 10, for example, its shape, mechanical characteristics of its maneuverability, and simulated position. In some embodiments, parameters of ablation power delivery are also provided as inputs: for example, frequency, power, duration of use, duty cycle, and/or phases of delivery through different electrodes.

Figure 11:
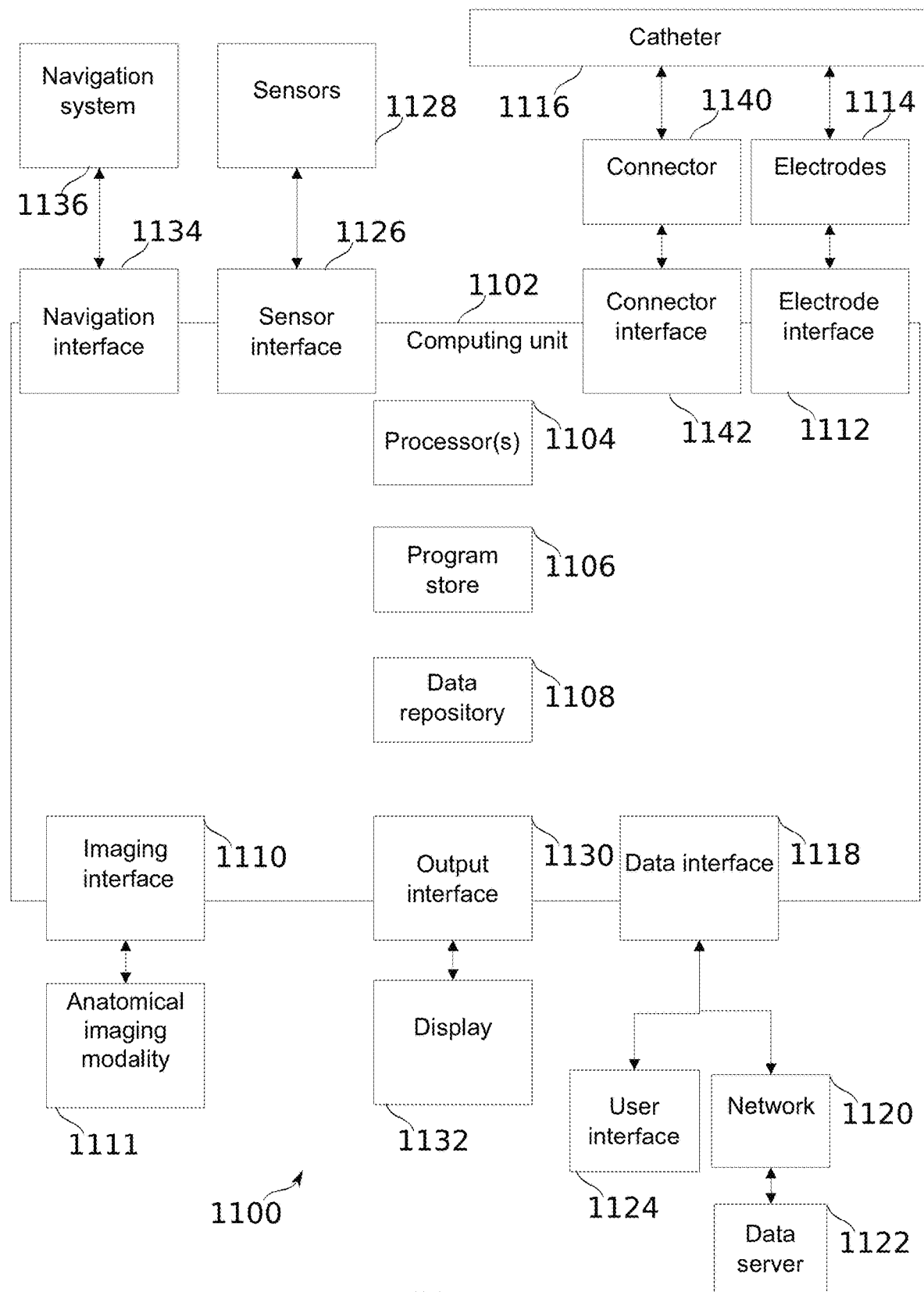
FIG. 11 is a block diagram of components of a system for tracking the position of an intra-body catheter, which is also optionally configured as a system for lesion planning, in accordance with some embodiments of the present disclosure.

In some embodiments, the system of FIG. 11 allows for an operator to monitor progress of an intra-body procedure according to a treatment plan, for example, lesioning along a line of planned ablation, with sufficient accuracy and precision to allow monitoring actual vs. planned ablations. Optionally, the system is configured to dynamically adjust the treatment plan according to the progress of the procedure. The system of FIG. 11 may execute, for example, the method of FIGS. 1A-1B and/or 10 (during a planning phase of a procedure); and/or FIG. 6 (during the procedure itself).

It is noted that the system of FIG. 11 may correct the location of the distal end of the catheter by separately and substantially simultaneously tracking the position of sensors, electrodes and/or other conducting ports on the distal end of the catheter.

As used herein, the terms sensor and electrode are sometimes interchangeable, for example, where referring to an element that performs measurements of one or more electrical properties (e.g., dielectric properties, conductance, impedance, voltage, current, and/or electrical field strength). For example, the electrodes may function as the sensors, such as by transmitting from one electrode to a second electrode, where the second electrode functions as a sensor. Impedance may be measured between respective electrode pairs, and/or between a designated electrode and a reference electrode (which may be located outside the body and/or within the body, such as on the catheter).

The system of FIG. 11 may provide additional features, for example, selection of the dielectric and/or thermal parameters (and/or elements that generate the dielectric and/or thermal parameters); estimation of contact force applied by the distal end of the catheter to the tissue wall, estimation of the lesion formation (e.g., size, volume and/or depth), estimation of tissue temperature, and/or mapping of fibrotic regions.

System 1100 may include a program store 1106 storing code, and a processor 1104 coupled to program store 1106 for implementing the stored code. Optionally, more than one processor may be used. It is noted that program store 1106 may be located locally and/or remotely (e.g., at a remote server and/or computing cloud), with code optionally downloaded from the remote location to the local location for local execution (or code may be entirely or partially executed remotely).

System 1100 may include an imaging interface 1110 for communicating with one or more anatomical imaging modalities 1111 that acquire a dataset of imaging data of a patient, for example, anatomical imaging data, e.g., a computer tomography (CT) machine, an ultrasound machine (US), a nuclear magnetic resonance (NM) machine, a single photon emission computed tomography (SPECT) machine, a magnetic resonance imaging (MRI) machine, and/or other structural and/or functional anatomical imaging modality machines. Optionally, imaging modality 1111 acquires three dimensional (3-D) data and/or 2-D data. It is noted that the anatomical images may be derived and/or acquired from functional images, for example, from functional images from an NM machine.

System 1100 may include an output interface 1130 for communicating with a display 1132, for example, a screen or a touch screen. Optionally, physically tracked location coordinates are displayed within a presentation of the dataset; for example, the 3-D acquired anatomical images are displayed on display 1132, with a simulation of the location of the distal end of the catheter within the displayed image based on the corrected location (examples of this are shown in FIGS. 8A-8B).

System 1100 may include an electrode interface 1112 for communicating with a plurality of physical electrodes 1114 and/or sensors (optionally, the electrodes serve as the sensors) located on a distal end portion of a physical catheter 1116 designed for intra-body navigation; for example: an electrophysiology (EP) ablation catheter, and/or another ablation catheter (e.g., a chemical ablation or injection catheter). Alternatively or additionally, system 1100 includes a navigation interface 1134 for communicating with a catheter navigation system 1136; optionally a non-fluoroscopic navigation system; optionally, an impedance measurement based system.

In some embodiments, intra-body navigation is performed based on body surface electrodes that receive and/or transmit current (e.g., alternating current) in different frequencies and/or different times between co-planar directions. Analysis of the electrical and/or thermal parameters obtained from the sensors of the catheter, separated into the different channels, is optionally used to estimate the location of each sensor relative to each body surface electrode. A calibration of the distances between the sensors (e.g., based on manufacturing specifications of the catheter, and/or measurements such as using fluoroscopy or other methods) may be performed.

Optionally, system 1100 includes a sensor interface 1126 for communicating with one or more sensors 1128, which may be in the body or external to the body; for example, for measuring electrical and/or thermal parameters, for example, impedance and/or conductivity and/or thermal conductivity and/or heat capacity and/or metabolic heat generation of the blood, the myocardium, and/or other tissues.

Optionally, system 1100 includes a data interface 1118, for communicating with a data server 1122, directly or over a network 1120, to acquire estimated dielectric and/or thermal tissue values for association with the acquired imaging dataset. Alternatively, the estimated dielectric and/or thermal values are stored locally, for example, on data repository 1108.

Optionally, a user interface 1124 is in communication with data interface 1118, for example, a touch screen, a mouse, a keyboard, and/or a microphone with voice recognition software.

Optionally, system 1100 (e.g., computing unit 1102) includes a connector 1140 connecting between catheter 1116 (e.g., RF ablation catheter, injection catheter) and a connector interface 1142 (and/or electrode interface 1112). Connector 1140 may be used to add additional features to existing catheters, such as off the shelf catheters, for example, RF ablation catheters, at least by acting as an input of signals communicated by the catheter for processing by system 1100. The signals communicated by the catheter are intercepted by circuitry within connector 1140 and transmitted to interface 1142 and/or 1112, without interfering with the signal transmission. The intercepted signals may be analyzed by system 1100, for example, to perform real-time tissue measurements (e.g., contact force, pressure, ablated volume and/or depth, temperature, and/or fibrosis mapping), to perform localization of the catheter, and/or to identify the type of the catheter.

It is noted that one or more of interfaces 1110, 1118, 1112, 1126, 1130, 1134, 1142 may be implemented, for example, as a physical interface (e.g., cable interface), and/or as a virtual interface (e.g., application programming interface). The interfaces may each be implemented separately, or multiple (e.g., a group or all) interfaces may be implemented as a single interface.

Processor 1104 may be coupled to one or more of program store 1106, data repository 1108, and interfaces 1110, 1118, 1112, 1126, 1130, 1134, 1142.

Optionally, system 1100 includes a data repository 1108, for example, for storing the dataset (e.g., imaging data of a patient), the simulation, received electrical and/or thermal parameters, and/or other data (such as: health record of a patient). The data may be displayed to a user (e.g., physician) before, during and after the procedure.

It is noted that one or more of processor 1104, program store 1106, data repository 1108, and interfaces 1110, 1118, 1112, 1126, 1130, 1134, 1142 may be implemented as a computing unit 1102, for example, as a stand-alone computer, as a hardware card (or chip) implemented within an existing computer (e.g., catheterization laboratory computer), and/or as a computer program product loaded within the existing computer.

Program store 1106 optionally includes code implementable by processor 1104 that represents a simulation tool and/or application that generates RF simulations (e.g., based on simulated generated fields) based on a provided dielectric map and/or other data.

Returning to FIG. 10: at 1002, a dataset of a body portion of a patient including anatomical imaging data of the patient (optionally 3-D data) is provided, for example, acquired from imaging modality 1111 (e.g., CT, MRI), retrieved from repository 1108, and/or acquired from an external server or other storage. Alternatively or additionally, the dataset is acquired and/or derived from a functional imaging modality, for example, NM and/or SPECT. For example, data from the NM modality may be used to infer the location of autonomous nervous system components (e.g., one or more ganglion plexi) designated for treatment on the dataset from the CT modality, for example, as described with reference to "BODY STRUCTURE IMAGING", International Publication No. WO2014/115148 filed Jan. 24, 2014, which is incorporated herein by reference in its entirety.

The data obtained from the CT machine (and/or other imaging devices) serves as a basis for geometrical structure and/or modeling of internal organs of the patient, for example, the organs are segmented using image segmentation code. The electrical and/or thermal properties and/or other values (e.g., mechanical, physiologic, other tissue related values) are associated with each organ, optionally according to the designated operational frequency used by the RF ablation catheter.

Optionally, the imaging dataset includes the target tissue for treatment in a catheterization procedure; for example, the heart. Optionally, the imaging dataset includes tissues surrounding the target tissue for simulation of the procedure, for example, a full body scan, a full thorax scan, a chest and abdominal scan, and/or a chest scan. For example, for an intra-cardiac ablation procedure, a full thorax scan may be performed.

Optionally, the imaging data is analyzed and/or processed to identify different types of tissues within the imaging data, for example, each pixel data or region is classified into a tissue type. Suitable classification methods include, for example, according to image segmentation methods, according to a predefined imaging atlas, and/or based on Hounsfield units.

Code stored, for example in program store 1106, implementable by processor 1104 accesses estimated dielectric and/or thermal parameter values, and associates each tissue type and/or pixel and/or region in the dataset with the estimated dielectric and/or thermal parameter values.

The dielectric and/or thermal parameter values may be obtained, for example, from a publicly available database (e.g., on data server 1122), calculated from a model, and/or based on empirically measured values from a sample of patients. It is noted that the estimated dielectric and/or thermal parameter values may reflect values that have not necessarily been measured for the patient being treated. In some embodiments, a 2-D or 3-D dielectric map of the region (e.g., organ) or a portion of the organ is created and optionally displayed to a user.

The dataset including anatomical image data associated with the dielectric and/or thermal parameter values may sometimes be referred to herein as a dielectric map. It is noted that the dielectric map may include dependencies of the dielectric parameter values on the thermal parameter values.

Optionally, the anatomical image (e.g., after segmentation) and the estimated dielectric and/or thermal parameter values or the 2-D or 3-D dielectric map are inputted to the simulation tool, which may be implemented as code stored in program store 1106 implementable by processor 1104, or as a separate unit (e.g., external server, hardware card, remotely located code implementable locally).

Optionally, the dataset is used to generate a simulation as part of a pre-planning phase, for example, as described with reference to FIGS. 1A-1B. The pre-planning phase simulates different parameters for the planned procedure, to help select one or more different parameters for the actual procedure, according to, for example, reduced error in tracking the location of the catheter, improved accuracy in tracking location of the catheter, selection of the treatment location of the catheter, and/or selection of ablation parameters and/or ablation lines according to a simulation of the ablation.

Optionally, the dielectric parameters include an impedance and/or conductive value of the respective tissue and/or tissue region. Optionally, information used in the simulation includes a contact force or other measure of contact (e.g. dielectric property contact quality assessment) between the ablation probe and target tissue.

It is noted that the patient may undergo imaging before the catheterization procedure, for example, as a separate outpatient procedure.

Optionally, the dataset after simulation is revised to include the imaging data and the one or more dielectric and/or thermal parameter values corresponding to different tissues and/or regions of the anatomical imaging data. The dielectric and/or thermal parameter value represents an initial estimated value, which may be adjusted based on real-time measurements obtained from the patient.

Optionally, the dataset is associated with additional data, for example, mechanical parameters (e.g., fibrosis map), physiological parameters (e.g., patient ECG patterns, patient body temperature), myocardial fiber orientation data, heart wall thickness data, and other tissue specific parameters. In some embodiments, the data set comprises characterization of an anisotropy of the tissue, for example, a structural anisotropy such as myocardial or other fiber orientation, and/or a functional anisotropy such as direction of perfusion and/or impulse propagation.

Optionally, the dataset is associated with additional data related to the medical state of the patient; for example, medications the patient is taking (e.g., which may affect the ionic concentration of the tissues of the patient, affecting the electrical and/or thermal parameters), the medical state of the patient (e.g., which may affect the anatomy of the patient), and a history of previous treatments (e.g., which may help predict the effects of the current treatment).

At block 1004 of FIG. 10, in some embodiments, code stored in data repository 1108 processes the dielectric map (i.e., the dataset) of block 1002, to generate a simulation. In some embodiments, the simulation simulates the navigation path during the procedure or part thereof, using a simulated catheter, and simulated applied electric parameters by simulated body surface electrodes (e.g., positioned on the skin of the patient).

Optionally, the simulation receives one or more of the following inputs, to generate the initial simulation and/or update the simulation (e.g., as in block 134 of FIG. 6): the anatomical model (e.g., obtained based on a CT and/or other imaging data of the patient), the dielectric map (initial or updated) which includes dielectric properties and/or thermal properties, fibrosis data, conductance map (e.g., from a stored location based on previous conductance mapping and/or real-time mapping), ablation catheter parameters (e.g., frequency, model, type, mechanical maneuvering properties, and/or electrodes positions), impedance measurements, thermal property measurements, and/or other data values.

The simulation may track the position (such as coordinates) of the simulated catheter within the dataset representing the body portion according to the simulated application of the electrical fields (or other electrical parameters, such as current, impedance, and/or voltage) within the body portion (i.e. based on the extra-body simulated electrodes). The simulation may simulate the measurements of the simulated applied electrical fields, optionally as measured by electrodes at a distal portion of the simulated catheter. In particular, the simulation may track thermal effects of the application of ablation energies to portions of the body visited by the catheter.

Optionally, the generated simulation includes a dataset of the coordinates (or other position data) of the simulated catheter within the dataset related to navigation of the catheter as part of the procedure.

Optionally, the simulation is performed at one or more operating frequencies, for example, when simulating a catheter ablation procedure. Exemplary simulation frequencies include: about 460 kilohertz (kHz), about 1 megahertz (MHz), about 12.8 kHz, or other frequencies. The simulation frequency is used to measure changes during the ablation process, and correct the ablation parameters accordingly, as described herein.

Optionally, the simulation includes coordinates in space which represent a simulation of electrodes and/or sensors that provide measurements of values of the electrical and/or thermal properties. The simulation of the measured values may be used, for example to simulate the measurement of induced currents. The simulation of the induced currents may reduce the number of time the simulation is run to below the number of sampling points in space, which reduces the required computational resources to perform the simulation.

Optionally, the simulation calculates the optimal position for a multi-electrode phased RF catheter, for example, to obtain the best real-time measurements, for example, with improved signal to noise, or reduced error.

Exemplary commercially available simulation tools that may be used as a framework for generating the simulation described herein include: Sim4Life (available from Zurich Med Tech), COMSOL Multiphysics®, and CST Design Studio™.

Figure 12:
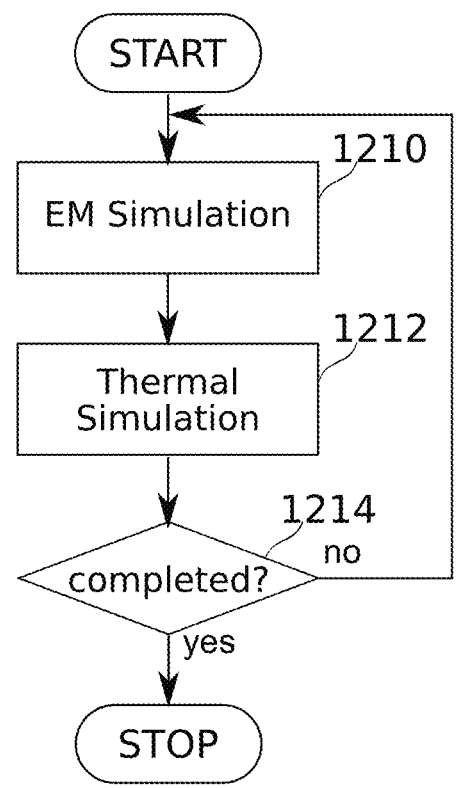
FIG. 12 is a flowchart of an exemplary method for generating the thermal component of the generated simulation, in accordance with some embodiments of the present disclosure.

Reference is now made to FIG. 12, which is a flowchart of an exemplary method for generating the thermal component of the generated simulation, in accordance with some embodiments of the present invention.

The flowchart begins, and at block 1210, in some embodiments, the electric properties of the catheterization procedure materials are set based on the received values, for example, for a certain catheter, at a certain angle, pressure, and operating frequency (e.g., when performing an ablation procedure and/or as part of a measurement process). The simulation is generated to simulate the electromagnetic fields on the catheter. The power density loss (PLD) pattern is optionally simulated.

At block 1212, in some embodiments, the thermal properties of the tissues and/or catheterization procedure are set based on the received values. The PLD pattern is optionally used as a heat source for generating the thermal property component of the generated simulation. The thermal properties are simulated over a period of time to obtain a temperature distribution pattern over the period of time; for example, based on the procedure. The period of time may represent a significant period of time, for example, based on cardiac output, based on the estimated time to navigate the catheter within the heart, and/or based on the time for performing an ablation.

The initial electrical and thermal property values are updated as a function of temperature based on the initial simulation. At block 1214, in some embodiments, a determination is made as to whether the simulation period is complete or not. If not, blocks 1210 and 1212 are iterated over again. Otherwise, the flowchart ends. The blocks may be iterated until a stop condition is met, for example, a desired accuracy and/or simulation time, and/or until the values remain unchanged within a tolerance requirement. Optionally, during each iteration, the simulation uses the values calculated using the earlier simulation, to improve the accuracy and/or resolution of the updated simulated values.

Referring now back to block 1004 of FIG. 10: optionally, the generated simulation includes determination of a power loss density pattern. The PLD pattern may be generated for the tissue targeted for (or currently being) treated using RF energy. The PLD pattern may be estimated in time and/or space. Alternatively or additionally, the simulation includes determination of a temperature pattern. The temperature pattern may be generated for the tissue targeted or (or currently being) treated using RF energy. The PLD pattern may be estimated in time and/or space. The PLD pattern may be calculated for multiple points, for each set of electrode location (e.g., using the coordinates according to the externally applied electromagnetic field), the pressured applied to the tissue wall, and the angle of the electrode relative to the tissue. The PLD pattern may be used in the generated simulation to guide the ablation treatment.

The PLD pattern, and/or gasification transition pattern, and/or temperature pattern may be used to update the simulated electric fields for correction of coordinates determined using real-time measurements of the externally applied electric fields. The PLD pattern, and/or gasification transition pattern, and/or temperature pattern may affect the electric and/or thermal properties of tissues, which may alter the real-time measurements of the electric field and/or real-time measurements of the dielectric, electric, and/or thermal properties.

The PLD pattern, and/or gasification transition pattern, and/or temperature pattern calculated as part of the generated simulation may use the corrected catheter coordinates (and/or simulated catheter coordinates, and/or measured catheter coordinates) as input of the location of the catheter.

The PLD pattern may be calculated using Equ. 1:

$$PLD = \frac{1}{2}(\sigma + \omega\varepsilon_0\varepsilon'')|E|^2 = \frac{1}{2}\sigma_e|E|^2 \qquad \text{(Equ. 1)}$$

where:
$|E|$ is the magnitude of E;
$\omega = 2\pi f$ where f denotes frequency in Hertz (Hz); and
$\sigma_e$ is an effective conductivity defined as $\sigma + \omega\varepsilon_0\varepsilon_e''$.

The temperature pattern may be calculated based on an estimation of the rise of temperature, which may be estimated according to the continuity equation (i.e., Equ. 2) that describes the simple case of electromagnetic heating where the temperature rises at a uniform rate:

$$\frac{\partial T}{\partial t} = \frac{PLD}{\rho c_p} \qquad \text{(Equ. 2)}$$

where:
$\rho$ denotes the density; and
$c_p$ denotes the specific heat.

Reference is now made to FIG. 13A, which is a graph depicting the calculated PLD pattern created by an electrode 1302 (e.g., RF ablation electrode(s)) in a tissue 1304, in accordance with some embodiments of the present invention. The PLD pattern may be calculated using Equ. 1. The PLD pattern may be used in the generated simulation described herein.

In the figure:

D denotes the ablation depth (in mm),

G denotes the gap between the end of the ablated depth and the opposite wall (in mm; generally, D+G represents the wall thickness of the tissue), V denotes the volume of ablated shape in $mm^3$. The top view of an exemplary ablation region may be modeled as an approximately elliptical shape, and the ablated volume as an approximate half-ellipsoid.

The ablation volume may be further denoted by:

L denoting the length in mm of the ablation region (e.g., one axis of the ellipsoid), and W denoting the width in mm of the ablation region (e.g., another axis of the ellipsoid).

Reference is now made to FIG. 13B, which is a graph depicting the calculated temperature pattern (in degrees Celsius) created by an electrode 1306 (e.g., RF ablation electrode(s)) in a tissue 1308, in accordance with some embodiments of the present invention. The temperature pattern may be calculated using Equ. 2. The temperature pattern may be used in the generated simulation described herein.

Optionally, the Gasification Transition (GS) of ablation using cryogenic energy at each possible ablation region is calculated. The GS may be calculated based on the location of each ablation region, the pressure, the angle of the catheter, and/or other values. Based on the generated simulation, the location, pressure, angle, and/or other values may be selected to achieve safe GS values, for example, according to a safety requirement.

Software Modules for Ablation Planning

Figure 14:
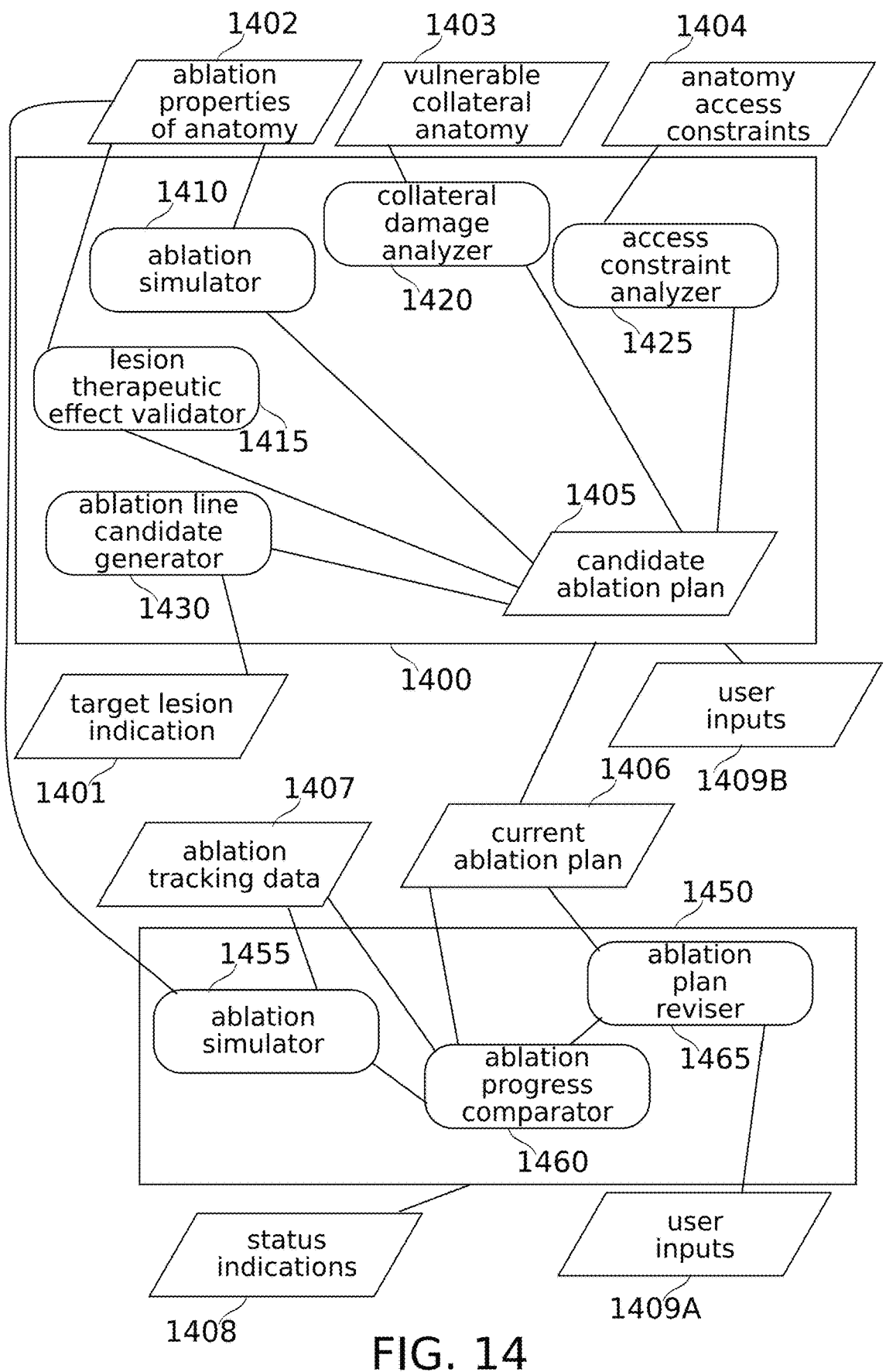
FIG. 14 is a schematic representation of software modules and associated data for use in ablation planning, according to some exemplary embodiments of the present disclosure.

Reference is now made to FIG. 14, which is a schematic representation of software modules and associated data for use in ablation planning, according to some exemplary embodiments of the invention.

In some embodiments of the invention, software for ablation planning comprises an initial planning module 1400, and/or an adaptive planning module 1450. In some embodiments, initial planning module 1400 is configured to carry out operations of flowchart FIG. 1B. In some embodiments, adaptive planning module 1450 is configured to carry out operations of flowchart FIG. 6. In some embodiments, data block 1401 corresponds to data defining a preliminary ablation line as in block 110 of FIG. 1B. In some embodiments, data blocks 1402, 1403, and 1404 correspond to data used in the operations of blocks 116, 112, and 114 of FIG. 1B.

In some embodiments, initial planning module 1400 comprises an ablation simulator, configured to receive data describing ablation properties of the patient-specific anatomy 1402, along with parameters of a candidate ablation plan 1405 (optionally supplemented by user input 1409B), and determine how the ablation plan will affect tissue of the patient. It should be understood that user input 1409B optionally influences the operation of any of the software modules of planning module 1400.

In some embodiments, ablation line candidate generator 1430 generates a candidate ablation plan 1405, based at least initially on target lesion indication 1401, and optionally on effects and/or constraints calculated by one or more of software modules 1410, 1415, 1420, and/or 1425.

In some embodiments, ablation simulator 1410 carries out simulation of the effects of a candidate ablation plan 1405 (optionally all at once and/or piecewise), based, for example, on thermal and/or dielectric simulation of ablation plan effects on patient anatomy and its properties with respect to ablation described by data block 1402.

In some embodiments, a lesion therapeutic effect validator 1415 is provided, which validates the degree to which simulated effects will meet the therapeutic goals of the planned therapy (based, for example, on the ablation properties of the patient-specific anatomy 1402). Examples of these goals (e.g. transmurality and avoidance of gaps) are described, for example, in relation to planning operations of FIG. 1B.

In some embodiments, a collateral damage analyzer 1420 is provided, which is configured to assess the potential for collateral damage of a candidate ablation plan 1405 (optionally, to provide suggested alternatives to the software system which reduce a risk for such damage), based on awareness of vulnerable collateral anatomy provided by data block 1403.

In some embodiments, access constraint analyzer 1425 is provided, which is configured to assess access constraints of a candidate ablation plan 1405 as being possible (for example, using a particular catheter and anatomical access route), relatively easy or hard, relatively reliable to perform, or otherwise evaluated. Optionally, access constraint analyzer 1425 is configured to provide suggested alternative ablation plan options to the software system which provide more preferred access to areas targeted for lesioning.

In some embodiments, the output of initial planning module 1400 comprises an initial version of current ablation plan 1406 (features of ablation plans are described, for example, in relation to FIGS. 1A-1B herein), which in turn serves as input to adaptive planning module 1450.

With reference now to adaptive planning module 1450: during a procedure for catheter ablation, in some embodiments, ablation simulator 1411 receives ablation tracking data 1407, including, for example positions of an ablation catheter, and/or data regarding operation of the ablation catheter. Optionally, ablation simulators 1411 and 1410 are implemented as the same module.

It should be understood that operations of the adaptive planning module 1400 are optionally monitored via status indications 1408 (e.g., displayed information) produced by the adaptive planning module 1400 and/or any of its subcomponents 1455, 1460, 1465. It should be understood that user inputs 1409A are optionally available to modify any suitable processing parameter and/or result produced by planning module 1400 and/or any of its subcomponents.

In some embodiments, ablation progress comparator 1430 receives the current ablation plan 1406, as well as ablation tracking data 1407 and/or simulated ablation information from ablation simulator 1411. Comparison of the actual record of events (from tracking data 1407), and/or the simulated effects of those events (from the ablation simulator 1411) is made to the current ablation plan 1406.

In cases where there are differences, in some embodiments, ablation plan reviser 1430 assesses what if anything, should be changed in the plan in order to achieve a successful result. Optionally, ablation plan reviser 1430 effectively comprises an implementation of initial planning module 1400 (and its inputs), suitably changed to support dynamic adaptation of the plan (e.g., allowing partial plan modifications, limiting modeling to what can be achieved in real time, etc.). In some embodiments, an updated plan becomes the new current ablation plan 1406. Optionally, the process of monitoring, comparing, and revising is iteratively performed.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method for planning an ablation plan of a target tissue in a patient, the method comprising:
   receiving data characterizing patient-specific anatomy comprising at least the target tissue, wherein the data include data on dielectric properties associated with the target tissue;
   simulating, by computer, one or more operations to lesion the target tissue, based on the received data, to create simulated results which indicate lesion effects on non-target tissue;
   evaluating, by a computer, one or more criteria on said simulated results, said one or more criteria including a criterion to avoid lesioning said non-target tissue that are adjacent to the target tissue;
   producing, by computer, a planned target form of the lesion, wherein the planned target form is produced based on said evaluating;
   producing, by computer, an ablation plan for producing the planned target form, the ablation plan comprising parameters of ablation as a function of structure thickness along the planned target form; and
   providing an indication of the planned target form.

2. The method of claim 1, wherein the data include data on thermal properties associated with the target tissue.

3. The method of claim 1, wherein the received data characterize geometry of the target tissue.

4. The method of claim 1, wherein the received data characterize a structural anisotropy as a function of position in the target tissue, and the ablation plan is produced based on consideration of the structural anisotropy.

5. The method of claim 4, wherein the anisotropy comprises an orientation of myocardial fibers in the target tissue.

6. The method of claim 1, wherein the received data characterize a position of at least one existing lesion in the target tissue, and the planned target form is adjusted to incorporate the at least one existing lesion.

7. The method of claim 1, wherein said one or more criteria comprises a criterion to block unwanted cardiac tissue conduction.

8. The method of claim 7, wherein the target tissue comprises a wall of an atrial heart chamber, and the planned target form of the lesion is produced for the blockage of cardiac muscle contractile impulses contributing to atrial fibrillation, based on the computer simulated results of one or more operations to lesion the target tissue.

9. The method of claim 1, wherein the simulated results comprise thermal simulation of the effect of lesioning on the patient-specific anatomy, based on thermal characteristics associated with the patient-specific anatomy.

10. The method of claim 1, wherein the planned target form of the lesion is produced for transmural ablation of the target tissue, while avoiding collateral damage to tissue in thermal contact with the target tissue.

11. The method of claim 1, wherein the simulated results comprise dielectric simulation of the effect of lesioning on the patient-specific anatomy, based on dielectric properties associated with the patient-specific anatomy.

12. The method of claim 1, wherein the target tissue comprises cardiac tissue and the non-target tissue comprises non-cardiac tissue.

13. The method of claim 1, comprising automatically adjusting the planned target form to avoid lesioning of the non-target tissue.

14. The method of claim 12, wherein the non-target tissue comprises at least one from the group consisting of: a portion of an esophagus, a portion of a phrenic nerve, and portion of a vascular root.

15. The method of claim 1, wherein the simulating produces simulated results simulating positions of a catheter used to perform the catheter ablation; and wherein the planned target form is produced based on regions of the target tissue which are accessible by the simulated positions.

16. The method of claim 15, wherein the simulated positions are constrained by mechanical properties of the catheter.

17. The method of claim 15, wherein the simulated positions are constrained by an anchor position applied to a portion of the catheter.

18. The method of claim 1, wherein the received data comprises 3-D imaging data of the patient-specific anatomy.

19. The method of claim 1, wherein said planned target form of the lesion is produced by selection.

20. The method of claim 1, comprising automatically modifying said one or more operations in response to said evaluating and wherein said producing comprises iteratively repeating said simulating, said evaluating and said modifying, automatically by computer.

21. A system for planning an ablation plan of a target tissue in a patient, the system comprising a processor configured to:
simulate, one or more operations to lesion the target tissue, based on data characterizing patient-specific anatomy comprising at least the target tissue, to create simulated results which indicate lesion effects on non-target tissue;
evaluate, one or more criteria on said simulated results, said one or more criteria including a criterion to avoid lesioning said non-target tissue that are adjacent to the target tissue; and
produce an ablation plan comprising a set of ablations applied along an extent of the target tissue;
wherein the data include data on dielectric properties associated with the target tissue; and
wherein the ablation plan is produced based on results of said evaluating.

22. The system of claim 21, wherein the data include data on thermal properties associated with the target tissue.

23. The system of claim 21, wherein the data characterize geometry of the target tissue, and the ablation plan describes the adjustment of parameters of the ablations as a function of geometry along a planned target form of the lesion.

24. The system of claim 21, wherein the simulated results comprise thermal simulation of the effect of lesioning on the patient-specific anatomy, based on thermal characteristics associated with the patient-specific anatomy.

25. The system of claim 21, wherein the processor is configured to adjust one or both of the extent of the set of ablations and ablation parameters along the set of ablations, to avoid lesioning of the non-target tissue.

26. The system of claim 21, wherein the processor is configured to apply a criterion to block unwanted cardiac tissue conduction and adjust one or more ablation parameters and/or one or more ablation location, accordingly.

\* \* \* \* \*